US008901042B2

(12) United States Patent
Ingolfsson et al.

(10) Patent No.: US 8,901,042 B2
(45) Date of Patent: Dec. 2, 2014

(54) HIGH THROUGHPUT SCREEN FOR MEASURING MEMBRANE EFFECTS

(75) Inventors: Helgi I. Ingolfsson, Groningen (NL); Olaf S. Andersen, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/389,147

(22) PCT Filed: Aug. 5, 2010

(86) PCT No.: PCT/US2010/044575
§ 371 (c)(1), (2), (4) Date: Apr. 5, 2012

(87) PCT Pub. No.: WO2011/017537
PCT Pub. Date: Feb. 10, 2011

(65) Prior Publication Data
US 2012/0184450 A1    Jul. 19, 2012

Related U.S. Application Data

(60) Provisional application No. 61/231,581, filed on Aug. 5, 2009.

(51) Int. Cl.
| | |
|---|---|
| *C40B 30/00* | (2006.01) |
| *G01N 21/00* | (2006.01) |
| *C40B 60/12* | (2006.01) |
| *G01N 33/92* | (2006.01) |
| *G01N 33/50* | (2006.01) |

(52) U.S. Cl.
CPC ............ *G01N 33/92* (2013.01); *G01N 33/5076* (2013.01); *G01N 2333/32* (2013.01)
USPC .......................................................... 506/7

(58) Field of Classification Search
CPC .......... C40B 60/00; C40B 30/00; C40B 60/12
USPC ................................................. 506/39, 41, 7
See application file for complete search history.

(56) References Cited

U.S. PATENT DOCUMENTS

| | | | |
|---|---|---|---|
| 2003/0068273 A1 | 4/2003 | Leyland-Jones | |
| 2005/0032246 A1* | 2/2005 | Brennan et al. | ............... 436/518 |
| 2008/0152640 A1 | 6/2008 | Prehm | |

FOREIGN PATENT DOCUMENTS

WO    WO 2006113550 A2 * 10/2006
WO    WO 2007089582 A2 *  8/2007

OTHER PUBLICATIONS

Andersen et al., Single-Molecule Methods for Monitoring Changes in Bilayer Elastic Properties, Methods in Molecular Biology, 2007, 400, 543-570.*
Bruggemann et al., Determination of the Molecularity of the Colicin E1 Channel by Stopped-Flow Ion Flux Kinetics, Proc. Natl. Acad. Sci. Biophysics, 1986, 83, 4273-4276.*
Ghosh et al., Theoretical Calculation of Absolute Radii of Atoms and Ions. Part 2. Ionic Radii, Int. J. Mol. Sci., 2003, 4, 379-407.*
Berberan-Santos et al., Mathematical Functions for the Analysis of Luminescence Decays with Underlying Distributions 1. Kohlrausch Decay Function (Stretched Exponential), Chemical Physics, 2005, 315, 171-182.*
Kelkar et al., The Gramicidin Ion Channel: A Model Membrane Protein, Biochimica et Biophysica Acta, 2007, 1768, 2011-2025.*
Greathouse, D. V. et al., "Design and Characterization of Gramicidin Channels" Methods Enzymol. (1999) pp. 525-550, vol. 294.
Ingolfsson, H. I. et al., "Screening for Small Molecules' Bilayer-Modifying Potential Using a Gramicidin-Based Fluorescence Assay" Assay and Drug Developmental Technologies (Aug. 2010) pp. 427-436, vol. 8, No. 4.
Lundbaek, J. A. et al., "Capsaicin Regulates Voltage-Dependent Sodium Channels by Altering Lipid Bilayer Elasticity" Mol. Pharmacol. (2005) pp. 680-689, vol. 68, No. 3.
Lundbaek, J. A. et al., "Lipid Bilayer Regulation of Membrane Protein Function: Gramicidin Channels as Molecular Force Probes" Review J R Soc Interface (Nov. 25, 2009).
Hwang, T-C. et al., "Genistein Can Modulate Channel Function by a Phosphorylation-Independent Mechanism: Importance of Hydrophobic Mismatch and Bilayer Mechanics" Biochemistry (2003) pp. 13646-13658, vol. 42.
Ingolfsson, H. I. et al., "Curcumin is a Modulator of Bilayer Material Properties" Biochemistry (2007) pp. 10384-10391, vol. 46.
Le Pioufle, B. et al., "Lipid Bilayer Microarray for Parallel Recording of Transmembrane Ion Currents" Analytical Chemistry (Jan. 1, 2008) pp. 327-332, vol. 80, No. 1.
Eskesen, K. et al., "Calcium-dependent Association of Annexins with Lipid Bilayers Modifies Gramicidin A Channel Parameters" Journal of Eur Biophys (2001) pp. 27-33, vol. 30.
Bruggemann, E. P. et al., "Determination of the Molecularity of the Colicin E1 Channel by Stopped-Flow ion flux Kinetics" Proc. Natl. Acad. Sci. USA (Jun. 1986) pp. 4273-4276, vol. 83.
Moore, H-P. et al., "Direct Spectroscopic Studies of Cation Translationcation by Torpedo Acetylcholine Receptor on a Time Scale of Physiological Relevance" Proc. Natl. Acad. Sci. USA (Aug. 1980) pp. 4509-4513, vol. 77, No. 8.
Ingolfsson, H. I., "Amphiphile Effects on Membrane Properties as Sensed by Membrane Spanning Proteins: Screening for Off-Target Drug Effects" A Dissertation Presented to the Faculty of the Graduate School of Cornell University in Partial Fulfillment of the Requirements for the Degree of Doctor of Philosophy (May 2010).
Lewis, B. A. et al., "Lipid Bilayer Thickness Varies Linearly with Acyl Chain Length in Fluid Phosphatidylcholine Vesicles" Journal of Molecular Biology (May 15, 1983) pp. 211-217, vol. 166, No. 2.

(Continued)

*Primary Examiner* — Maria Leavitt
*Assistant Examiner* — Amy M Bunker
(74) *Attorney, Agent, or Firm* — Scully, Scott, Murphy & Presser, P.C.

(57) ABSTRACT

The invention relates to assays for measuring the effect of a inactive test substance on a lipid bilayer, kits for measuring the effects of test substances on lipid bilayers and an apparatus for performing a high through-put assay that measures the effect of test substances on a lipid bilayer.

16 Claims, 10 Drawing Sheets

(56) References Cited

OTHER PUBLICATIONS

Rusinova, R. et al., "Thiazolidinedione Insulin Sensitizers Alter Lipid Bilayer Properties and Voltage-dependent Sodium Channel Function: Implications for Drug Discovery" J. Gen. Physiol. (Aug. 2011) pp. 249-270, vol. 138, No. 2.

Andersen, O. S., et al., "Single-Molecule Methods for Monitoring Changes in Bilayer Elastic Properties" Methods in Molecular Biology (Aug. 30, 2007) pp. 543-570, vol. 400.

Lundbaek, J., "Regulation of Membrane Protein Function by Lipid Bilayer Elasticity—a Single Molecule Technology to Measure the Bilayer Properties Experienced by an Embedded Protein" Journal of Physics: Condensed Matter (2006) pp. S1305-S1344, vol. 18.

Garcia, A. M., "Determination of Ion Permeability by Fluorescence Quenching" Methods in Enzymology (1992) pp. 501-510, vol. 207.

Läuger, P. et al., "Electrical properties of bi-molecular phospholipid membranes." Biochim. Biophys. Acta (1967) pp. 20-32, vol. 135.

Finkelstein, A. et al., "Permeability and electrical properties of thin lipid membranes" J. Gen. Physiol. (1968) pp. s145-s172, vol. 52.

Myers, V.B. et al., "Ion transfer across lipid membranes in the presence of gramicidin A. II. Ion selectivity" Biochim. Biophys. Acta (1972) pp. 313-322, vol. 274.

Soucková et al. "On GC/MS in phospholipid research I: determination of fatty acid profile and phosphorus content" AUPO Chemica, 2:1-7, 2011.

* cited by examiner

SEQUENCE LISTING

```
<160> NUMBER OF SEQ ID NOS: 1

<210> SEQ ID NO 1
<211> LENGTH: 15
<212> TYPE: PRT
<213> ORGANISM: Bacillus brevis
<220> FEATURE:
<221> NAME/KEY: MISC_FEATURE
<222> LOCATION: (1)..(1)
<223> OTHER INFORMATION: Xaa is formyl-L-Val
<220> FEATURE:
<221> NAME/KEY: MISC_FEATURE
<222> LOCATION: (3)..(3)
<223> OTHER INFORMATION: Xaa is L-Ala
<220> FEATURE:
<221> NAME/KEY: MISC_FEATURE
<222> LOCATION: (4)..(4)
<223> OTHER INFORMATION: Xaa is D-Leu
```

```
<220> FEATURE:
<221> NAME/KEY: MISC_FEATURE
<222> LOCATION: (5)..(5)
<223> OTHER INFORMATION: Xaa is L-Ala
<220> FEATURE:
<221> NAME/KEY: MISC_FEATURE
<222> LOCATION: (6)..(6)
<223> OTHER INFORMATION: Xaa is D-Val
<220> FEATURE:
<221> NAME/KEY: MISC_FEATURE
<222> LOCATION: (7)..(7)
<223> OTHER INFORMATION: Xaa is L-Val
<220> FEATURE:
<221> NAME/KEY: MISC_FEATURE
<222> LOCATION: (8)..(8)
<223> OTHER INFORMATION: Xaa is D-Val
<220> FEATURE:
<221> NAME/KEY: MISC_FEATURE
<222> LOCATION: (9)..(9)
<223> OTHER INFORMATION: Xaa is L-Trp
<220> FEATURE:
<221> NAME/KEY: MISC_FEATURE
<222> LOCATION: (10)..(10)
<223> OTHER INFORMATION: Xaa is D-Leu
<220> FEATURE:
<221> NAME/KEY: MISC_FEATURE
<222> LOCATION: (11)..(11)
<223> OTHER INFORMATION: Xaa is L-Trp
<220> FEATURE:
<221> NAME/KEY: MISC_FEATURE
<222> LOCATION: (12)..(12)
<223> OTHER INFORMATION: Xaa is D-Leu
<220> FEATURE:
<221> NAME/KEY: MISC_FEATURE
<222> LOCATION: (13)..(13)
<223> OTHER INFORMATION: Xaa is L-Trp
<220> FEATURE:
<221> NAME/KEY: MISC_FEATURE
<222> LOCATION: (14)..(14)
<223> OTHER INFORMATION: Xaa is D-Leu
<220> FEATURE:
<221> NAME/KEY: MISC_FEATURE
<222> LOCATION: (15)..(15)
<223> OTHER INFORMATION: Xaa is L-Trp-ethanolamine

<400> SEQUENCE: 1

Xaa Gly Xaa Xaa Xaa Xaa Xaa Xaa Xaa Xaa Xaa Xaa Xaa Xaa Xaa
1               5                   10                  15
```

US 8,901,042 B2

HIGH THROUGHPUT SCREEN FOR MEASURING MEMBRANE EFFECTS

CROSS-REFERENCE TO RELATED APPLICATION

This application claims the benefit of priority of U.S. Provisional Application 61/231,581, filed Aug. 5, 2009, the content of which is incorporated herein by reference.

GOVERNMENT FUNDING

This invention was made with Government support under Grant Number GM21342 awarded by NIH/NIGMS. The United States Government has certain rights in the invention.

BACKGROUND

The classical, somewhat simplistic, view of the lipid bilayer component of biological membranes is a flexible selectively permeable barrier that separates different cellular compartments. More recently it has been shown that the lipid bilayer is dynamic and actively involved in membrane protein localization and function. A typical membrane contains over 200 distinct types of lipids and changes in bilayer composition can regulate numerous biological functions.

The lipid bilayer is involved in regulating membrane protein function because the bilayer is coupled to its embedded membrane proteins by hydrophobic interactions; the hydrophobic core of the bilayer shields the hydrophobic surface of the membrane proteins and vice versa. The shielding of the hydrophobic surfaces leads to hydrophobic adaptation of the relatively soft bilayer to the more rigid protein. This adaptation incurs an energetic cost, meaning that the hydrophobic coupling between membrane proteins and the host bilayer causes the equilibrium distribution between different membrane protein conformational states to depend on the bilayer's ability to adapt to the transmembrane hydrophobic domains off these different states. Therefore, changes in bilayer composition and material properties can modify membrane protein function—and it is well-established that experimental maneuvers that change the lipid bilayer hydrophobic thickness or monolayer curvature, e.g. by altering acyl chain length or lipid head group size, cause changes in protein function.

The bilayer's collective properties are determined not only by the lipid composition but also by the proteins and amphipathic molecules (amphiphiles) imbedded in the hydrophobic continuum.

Amphiphiles can accumulate at the cell membranes' bilayer/solution interface and thereby change the bilayer properties. A large portion of commercially available drugs are amphiphiles, and it long has been known that many drugs are membrane modulators—meaning that they, in addition to binding to their cognate protein binding sites, adsorb to the bilayer/solution interface to alter bilayer properties. In fact, many drugs and other molecules that are used to manipulate biological functions modify bilayer collective properties at physiologically/pharmacologically relevant concentrations to such an extent as to alter membrane protein function (such as genistein, neurotoxins, capsaicin, butanedione monoxime, anti-fusion peptides, curcumin, and poly-unsaturated fatty acids).

This is important because many new drug leads are amphiphiles, and they seem to be increasingly hydrophobic in nature. That is, many current drug leads have physico-chemical properties that are likely to make them potent modifiers of bilayer collective properties. This means that these compounds are likely to alter the function of a wide variety of membrane proteins, in addition to their desired target(s).

Side effects caused by high doses of these drugs therefore can be due to their effect on the bilayer collective properties. This raises questions as to which drugs and at what concentrations will alter lipid bilayer properties sufficiently to promiscuously alter membrane protein function.

Current drug development relies heavily on high throughput screening for drug lead discovery. Large libraries of millions of small molecules are commonly screened for a desired function often resulting in thousands of potential leads. These molecules need to be further screened to verify their specific interaction with the drug target and their suitability as potential drugs.

There are a number of methods available to measure bilayer collective properties, including: small-angle x-ray scattering (for measuring changes in bilayer thickness and intrinsic lipid curvature), membrane inserted fluorescent probes (to measure changes in the order and dynamics of the bilayer hydrophobic core) and micropipette aspiration methods (for measuring changes in bilayer elasticity). These methods usually detect changes in just a specific subset of bilayer properties under rather non-physiological conditions, and it may be difficult to relate the measured changes to changes in membrane protein function.

A broadly applicable method for determining changes in membrane collective properties in physiological systems is the gramicidin A (gA) channel-based method, because the channels' structural simplicity minimizes the risk that the changes in channel function are due to direct channel-drug interactions. gA single-channel electrophysiology has been studied extensively to examine many different questions, specifically, to measure non-specific membrane effects of marketed and investigational drugs. Using the single-channel technique, changes in bilayer collective properties have been measured for a variety of lipid compositions and after the addition of different small molecules. When working at the single-channel level, it is possible to directly monitor different gA channel properties. But to calculate population averages, it is necessary to collect hundreds of stochastic single channel events for each condition. Additionally the gA signal channel events are tiny (conductance is in the pA range) requiring specialized electrophysiological equipment to achieve the necessary signal-to noise ratio. To successfully test just one compound and/or lipid composition may take a highly trained person days, if not weeks, of collecting/analyzing single channel events. Only a limited number of molecules therefore have been tested in detail with the gA channel method, because the assay requires measurement of large quantities of single channel events, requiring an extensive experimental effort to test a single condition.

SUMMARY OF THE INVENTION

The invention is directed to an assay for measuring the effect of a test substance on a lipid bilayer, kits for measuring the effects of test substances on lipid bilayers, and an apparatus for performing a high throughput assay that measures the effect of test substances on a lipid bilayer.

In one embodiment, the invention provides an assay for measuring the effect of a test substance on a lipid bilayer. The assay includes the steps of providing vesicles composed of a lipid bilayer, a pair of an indicator and a monovalent cation, and gramicidin, wherein the vesicles contain one member of the indicator-cation pair, and comprise gramicidin in the lipid bilayer, and wherein at least some molecules of gramicidin present in the lipid bilayer are in the monomeric form; treating at least a portion of the vesicles with the test substance; exposing the vesicles to a solution containing the other member of the indicator-cation pair, wherein movement of the cation across the lipid bilayer through a conducting gramicidin channel causes the indicator to generate a detectable signal; comparing the detectable signal generated from the vesicles treated with the test substance with the detectable signal generated from the vesicles not treated with the test substance; and determining the effect of the test substance on the lipid bilayer based on the comparison.

In another embodiment, the invention provides kits for measuring the effect of a test substance on a lipid bilayer. In a specific embodiment, the kit contains lipids for forming bilayer vesicles, a pair of an indicator and a monovalent cation, gramicidin, and instructions to form vesicles from the lipids, to introduce one member of the indicator-cation pair into the vesicles, and to introduce gramicidin into the lipid bilayer of the vesicles. In another specific embodiment, the kit contains vesicles composed of a lipid bilayer, and a pair of an indicator and a monovalent cation, wherein the vesicles contain one member of the indicator-cation pair, gramicidin, and instructions to dope the vesicles with gramicidin. In still another specific embodiment, the kit includes vesicles composed of a lipid bilayer, and a pair of an indicator and a monovalent cation, wherein the vesicles contain one member of the indicator-cation pair and doped with gramicidin.

In a further embodiment, the invention provides an apparatus for performing a high throughput assay that measures the effect of test substances on a lipid bilayer. The apparatus includes: at least one chamber or separate chambers to hold the following: gramicidin-loaded vesicles encompassing an indicator, a test substance, and gramicidin channel permeable cations; means to move contents of the chambers; means to combine the gramicidin-loaded vesicles encompassing an indicator and the test substance to form a mixture, and to incubate the mixture; means to rapidly mix the incubated mixture with the gramicidin channel permeable cations; and means to detect the signal generated from the rapid mixing and means to process and analyze the detected signal.

Figure 1:
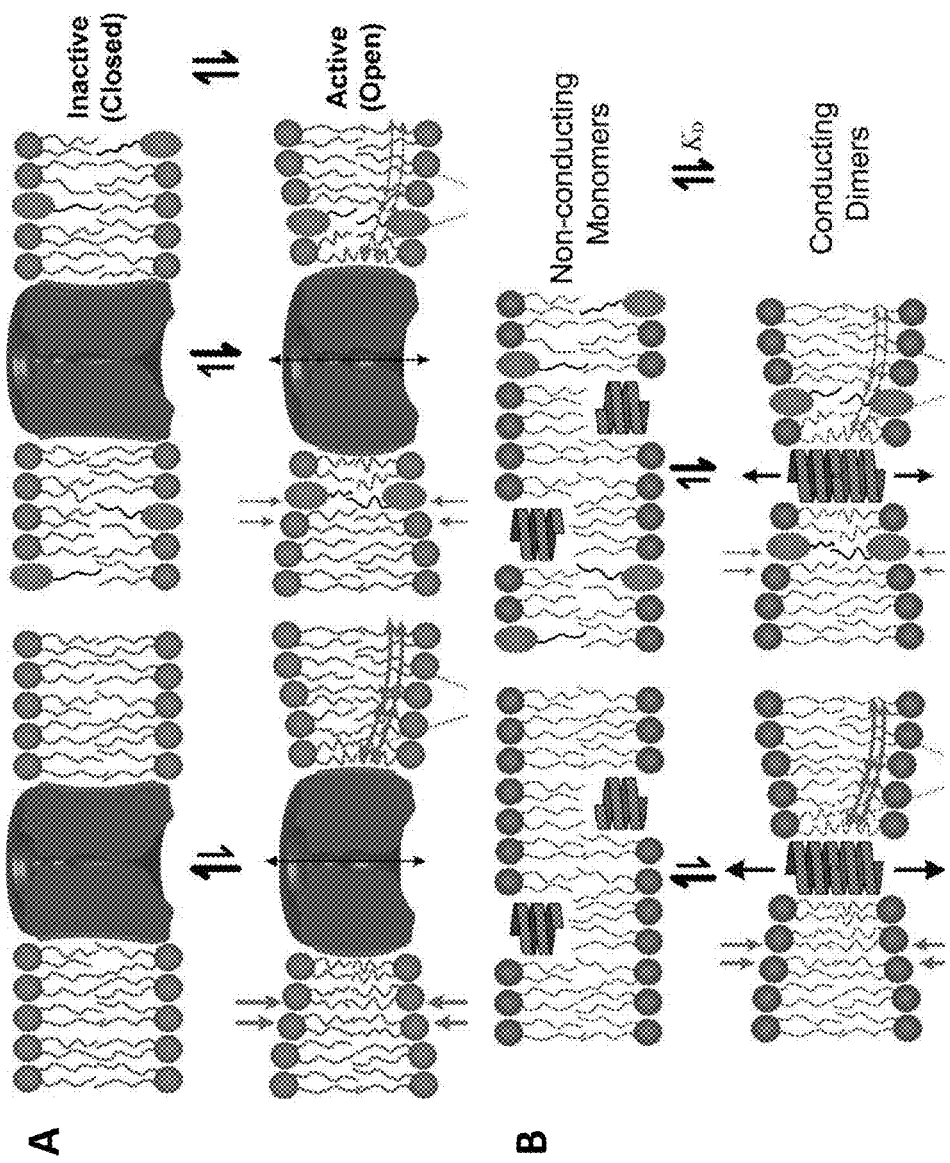
FIG. 1. Amphiphiles can affect protein function without direct binding. The hydrophobic coupling between membrane proteins and their host bilayer provides for energetic coupling of the protein conformational preference to bilayer material properties. For the case of ion channels, with a difference in hydrophobic length between the two states, the bilayer has to deform locally to accommodate the channels conformational change. The energetic cost of deforming the bilayer will influence the equilibrium distribution between the states. Because absorbed amphiphiles can alter the bilayer material properties (compression and/or bending moduli) they can alter protein function without binding to the protein. This is depicted for a generic membrane protein/ion channel in FIG. 1A and for gramicidin channels in FIG. 1B.

10.01 A multi-well tray containing test chemicals and controls.

10.02 Container with a solution comprising indicator-loaded LUVs that have been doped with gramicidin.

10.03 Container with a solution comprising indicator-loaded LUVs without gramicidin.

10.04 Container with a solution comprising gramicidin channel permeable cations that interact with the indicator.

10.05 Container with buffer.

10.06 Multi-well rotary.

10.07 Dispenser that can transfer samples from the rotary (10.06) into 10.11.

10.08 Three-way injection valve that can dispense solutions from either 10.04 or 10.05 into 10.10.

10.09 Robotic pipetter/mixer that can fetch liposome solution from either 10.02 or 10.03 and any compound from 10.01 and mix them into a well in 10.06.

10.10 Injector for the rapid mixing into the recording system (10.12).

10.11 Injector for the rapid mixing into the recording system (10.12).

10.12 Rapid mixing and recording system.

10.13 Workstation that controls 10.06, 10.07, 10.08, 10.09, 10.10, 10.11 and 10.12, and that receives, analyses, and presents data from the rapid mixing and recording system.

DETAILED DESCRIPTION

This invention provides a high-throughput assay that measures the lipid bilayer-modifying effects of test compounds based on detecting signals, which correlate with the number of bilayer-spanning, conducting gramicidin channels in the lipid bilayer. The changes in detected signals reflect changes in the collective properties of lipid bilayers, which could influence the function of proteins in the bilayer.

The present assay is useful for assessing the lipid bilayer-modifying effects of many kinds of test substances, including but not limited to: libraries of drugs used in human or veterinary clinical medicine; drugs that have been withdrawn because of unacceptable side effects; chemical libraries; chemicals on the pathway from hits to leads to investigational drugs. The present assay can also be used to evaluate substances, pure, compounded, or complex, that are being investigated for potential toxicity, such as pesticides, insecticides, dietary supplements, food ingredients, cosmetic ingredients, plant samples, plant extracts, insect, and animal toxins.

By "bilayer-modifying effect" is meant herein that a test compound alters the properties of a lipid bilayer and indirectly the functions of proteins embedded in or associated with the bilayer, as opposed to affecting the proteins through direct interactions (e.g., binding) with the proteins. A test compound can have a bilayer-modifying effect that increases the bilayer deformation energy associated with formation of ion-conducting gA channels (or making the bilayer stiffer), in which case the formation of conducting gA channels is slowed—and their dissociation is accelerated—leading to fewer conducting gA channels per membrane area (per unit time). Alternatively, a test compound can have a bilayer-modifying effect that decreases the bilayer deformation energy associated with formation of ion-conducting gA channels (or making the bilayer softer), in which case the formation of conducting gA channels is accelerated—and their dissociation is slowed—leading to more conducting gA channels per unit membrane area (per unit time). Both of these bilayer-modifying effects can be detected and quantified using the assay of the present invention.

Assay Basis and Design

The high throughput assay of the invention is principally based on detecting signals that correlate with the surface density of ion-conducting gramicidin (gA) channels present in a lipid bilayer. The gA channel surface density in turn reflects the collective properties of the lipid bilayer and changes in the lipid bilayer properties caused by a test compound therefore result in changes in the density of ion-conducting gramicidin (gA) channels, and hence changes in the signals detected.

Ion conducting gramicidin (gA) channels form by the transmembrane dimerization of two non-conducting monomers. The gramicidin channels are sensitive to their membrane environment; changes in lipid bilayer properties therefore can be reflected in modified channel activity.

A generic membrane protein/ion channel is depicted in FIG. 1A and FIG. 1B shows a bilayer-incorporated gA channel. The hydrophobic coupling between the bilayer and membrane proteins hydrophobic surface effectively ties the energetics of protein conformational change to the cost of membrane deformation. Changes in lipid bilayer properties can affect the energetic cost of the membrane deformation, and as membrane proteins' hydrophobic surface can differ between one conformational change over another, the change in the membrane deformational energy can vary too. FIG. 1 shows examples of an ion channels with a shorter hydrophobic length (l) in the open conformation than in the closed one; changing lipid bilayer properties such that bilayer compression will be less costly, will reduce the cost of the membrane deformation for the open state while having little effect on the bilayer protein adaptation for the closed state. Changes in lipid bilayer properties can thus affect not only the energetics but also the kinetics of protein conformational changes.

gA single-channel electrophysiology has been used to measure changes in bilayer collective properties caused by a variety of lipid compositions. When working at the single-channel level, it is possible to directly monitor different gA channel properties such as frequency of formation, lifetime and conductance. To calculate population averages, however, it is necessary to collect hundreds of stochastic single channel events for each condition. Additionally the gA signal channel events are tiny (conductance is in the pA range) requiring specialized electrophysiological equipment to achieve the necessary signal-to noise ratio. To successfully test one compound and/or lipid composition, it may take a highly trained person days or even weeks of collecting/analyzing single channel events.

In contrast, in the assay of the present invention, the bilayer-modifying effects of a test compound are measured by probing for changes in the surface density of conducting gA channels, which allow for estimates of drug-induced changes in the channel's dimerization constant ($K_D$). $K_D$ varies as a function of changes in the bilayer deformation energy associated with channel formation. Because reversibly-adsorbing amphiphiles change the lipid bilayer material properties, and therefore the bilayer deformation energy associated with channel formation, it becomes possible to detect drug-induced changes in bilayer properties. Thus, in essence, the high throughput assay of the invention is based on detecting in a single measurement, the density of conducting gA channels present in a lipid bilayer. The present assay provides good agreement with previous electrophysiological results achieved by using single-channel experiments, yet is more efficient. An initial configuration of the assay has permitted testing dozens of samples a day, which is two to three orders of magnitude faster than was previously possible using single-channel experiments. Given an automated stopped-flow spectrophotometer, hundreds to thousands of compounds a day can be tested for their bilayer modifying effects.

In certain embodiments of the invention, the assay is designed to monitor changes in gramicidin dimerization directly, by using gramicidin analogues that have been labeled with a suitable fluorescence donor/acceptor pair, such that changes in dimerization is detected by monitoring the changes in the fluorescence resonance energy transfer.

In other embodiments of the invention, the assay is designed to monitor changes in gramicidin dimerization indirectly based on detecting movement of cations through conducting gA channels. When gramicidins dimerize to form conducting channels, they allow for movement of monovalent cations below a certain size (radius ~2 Å). Therefore, by providing an indicator-monovalent cation pair, where the indicator generates a detectable signal upon movement of the cation through conducting gA channels, the signals detected can be correlated with the number of ion-conducting gA channels.

In one embodiment, the assay employs a pair of an indicator and a monovalent cation, which are separated by a vesicle lipid-bilayer membrane incorporated with gA molecules. The monovalent cation is below the critical size (radius ~2 Å) that allows for movement through a conducting gA channel. Movement of the monovalent cation through conducting gA channels in the bilayer triggers the indicator on the other side of the bilayer to generate a detectable signal. The phrase "generating a detectable signal" is used in a general sense, and can include quenching of a fluorescent signal.

In the event that a compound changes material properties of the lipid bilayer, and hence the bilayer deformation energy associated with formation of ion-conducting gA channels, the channel's dimerization constant will change, and consequently the average density of conducting gA channels in the lipid-bilayer will change, which in turn will affect the movement of the monovalent cation and therefore the detectable signal being generated by the indicator. Thus, by comparing the signal generated by the indicator in the presence of a test compound with the signal generated by the indicator in the absence of the test compound, one can ultimately make a determination as to whether or not the test compound has a bilayer-modifying effect.

Reagents and Kits

In those embodiments where changes in gramicidin dimerization are monitored directly, gramicidin analogues that have been labeled with a suitable fluorescence donor/acceptor pair are used such that changes in dimerization are detected directly by monitoring the changes in the fluorescence resonance energy transfer.

Specific examples of such fluorescent-labeled gramicidins include 5-(dimethylamino)naphthalene-1-sulfonyl (dansyl)- and 4-(diethylamino)-phenylazobenzene-4-sulfonyl (DPBS)-labeled gramicidin C—in gramicidin C the tryptophan on position 11 in gramicidin A has been replaced by tyrosine.

In other embodiments where changes in gramicidin dimerization are monitored indirectly, lipid vesicles, a pair of an indicator and a monovalent cation, and a preparation of gramicidins, are provided and used in the assay.

For the indicator-monovalent cation pair implementation, the cation is below the critical size (radius ~2 Å) and permeates through a conducting gA channel. The indicator and the monovalent cations are initially separated by the vesicle lipid-bilayer membrane. Movement of the monovalent cations through conducting gA channels in the bilayer then triggers the indicator on the other side of the bilayer to generate a detectable signal. In some embodiments, the indicator is loaded into the interior part of the vesicles, and the monovalent cation is provided in an extravesicular solution. In other embodiments, the monovalent cation is loaded into the interior part of the vesicles, and the indicator is provided in an extravesicular solution.

Indicators suitable for use in the present invention can be a water-soluble fluorophore, where the fluorescence is quenched by the monovalent cation moved through a conducting gA channel. Indicators can also be a conventional indicator, such as a pH- or cation-sensitive fluorophore, where the fluorescence signal is generated when the ion moves across the vesicle membrane (to bind to the indicator). In principle, it is not necessary to have a fluorescent indicator; changes in absorbance could serve the same purpose.

In one embodiment, the cation sensitive fluorophore 8-aminonaphthalene-1,3,6-trisulfonic acid disodium salt (ANTS) is used as the indicator. In other embodiments, other indicators can be used, e.g., fluorescein-5-(and -6)-sulfonate, benzothiazole coumarin acetate, sodium binding benzofuran isophthalate (SBFI), sodium green and potassium binding benzofuran (PBFI), among others (Minta et al., *J. Biol. Chem.* 264:19449-57 (1989); Szmacinski et al., *Anal. Biochem.* 250:131-8 (1997); Meuwis et al., *Biophys. J.* 68:2469-73 (1995)).

The monovalent cation suitable for use in the present invention includes any monovalent cation that is of a size (e.g., smaller than about 2 Å in radius) that allows for movement through a conducting gA channel, and subsequently triggers the indicator to generate a detectable signal. In a specific embodiment, Tr is the choice of monovalent cation. In other embodiments, the monovalent cation used can be $Na^+$, $K^+$ and $Cs^+$, among others suitable cations.

A number of pairs of indicators and cations are suitable for use in the present invention. Some examples of these pairs include the pair of fluorescein-5-(and -6)-sulfonate indicator to $H^+$ cation, the pair of benzothiazole coumarin acetate indicator to Tr cation, the pair of sodium green indicator to $Na^+$ cation, the pair of SBFI indicator to $Na^+$ cation, the pair of $PBFI^+$ indicator to $K^+$ cation and the pair of ANTS indicator to $Tl^+$ cation, among other suitable pairs of indicators and cations.

Figure 2:
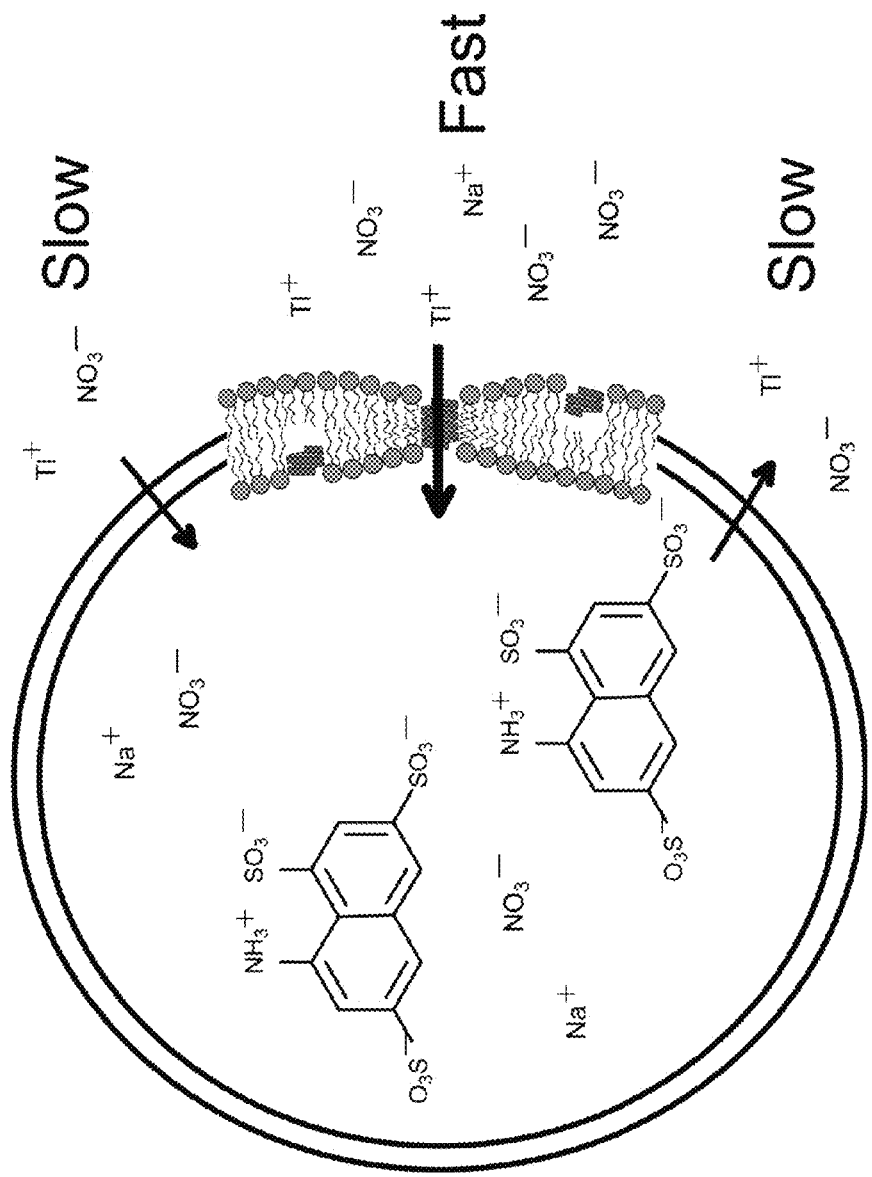
FIG. 2. Diagram of a LUV filled with the fluorophore 8-aminonaphthalene-1,3,6-trisulfonic acid disodium salt (ANTS) and doped with gA. $Tl^+$ and ANTS cross the lipid bilayer poorly, whereas gA channels are quite permeable to $Tl^+$. Therefore, the rate of $Tl^+$ influx into the vesicle, and consequently the rate of ANTS fluorescence quenching, is proportional to the number of (bilayer-spanning) conducting gA channels in the LUV. The "expanded" view on the right side of the vesicle shows the two major forms of gA, monomeric non-conducting and dimeric conducting states.

FIG. 2 depicts a LUV doped with gA where the fluorophore/quencher pair is ANTS/$Tl^+$, and the LUV is loaded with ANTS. Tr and ANTS cross the lipid bilayer poorly, whereas gA channels are $Tl^+$ permeable. The rate of Tr influx into the vesicle, and thus the rate of fluorescence quenching, are proportional to the number of (bilayer-spanning) conducting gA channels in the LUV. The "expanded" view to the right shows a lipid bilayer segment with the two major gA forms: nonconducting monomers and conducting dimers.

Lipid vesicles suitable for use in the present assay can be formed by using any appropriate lipids, including those available from commercial sources. Some non-limiting examples of lipids that can be used, with or without cholesterol, include di-$C_{22:1}$-PC (PC stands for phosphatidylcholine and the $C_{22:1}$ stands for the number of carbons in the fatty acid chain: the number of saturated bonds), di-$C_{20:1}$-PC, di-$C_{18:1}$-PC, 1-$C_{16}$-2-$C_{18:1}$-PC, as well as di-$C_{18:1}$-PE (PE stands for phosphatidylethanolamine) and di-$C_{18:1}$-PS (PS stands for phosphatidylserine), and analogues or combinations thereof, as well as lipid mixtures extracted from various biological sources.

Specific types of lipids can be chosen for the formation of lipid vesicles to match the gramicidin used for the assay in order to control the basal gA channel activity to such a range that allows for detection of changes. Gramicidin channels form by a trans-bilayer dimerization of two non-conducting subunits that reside in each bilayer leaflet. The gramicidin dimerization constant varies as a function of the channel-bilayer hydrophobic mismatch, the bilayer elastic moduli and the intrinsic curvature of the lipids used to form the vesicles. It is possible to vary the hydrophobic mismatch by changing either the channel length, which can be done by synthesizing gramicidin analogues of different lengths (Hwang et al., *Bio-* chemistry 42:13646-58 (2003); Ingólfsson et al., *Biochemistry* 46:10384-91 (2007); Greathouse et al., *Methods Enzymol.* 294:525-50 (1999)) or the bilayer thickness, which can be done by using phospholipids having different acyl chain length (see, e.g., Lewis et al., *J. Mol. Biol.* 166:211-7 (1983)). The bilayer elastic moduli can be modulated by adding cholesterol to the vesicle-forming lipid mixture, or by changing lipid acyl chain unsaturation. Additionally, the intrinsic curvature can be modified by changing the phospholipid head groups. Because amphiphiles usually make the bilayer softer, meaning that they shift the monomer⇌dimer equilibrium toward the right, the ability to detect whether a given amphiphile alters lipid bilayer properties is made easier if the vesicle lipid composition and gramicidin are chosen such that the monomer⇌dimer equilibrium before the amphiphile addition of is shifted toward the left.

In specific embodiments, the lipids are selected such that the bilayer formed has a thickness that is about 1 nm thicker than the length of a conducting gA channel.

Figure 9:
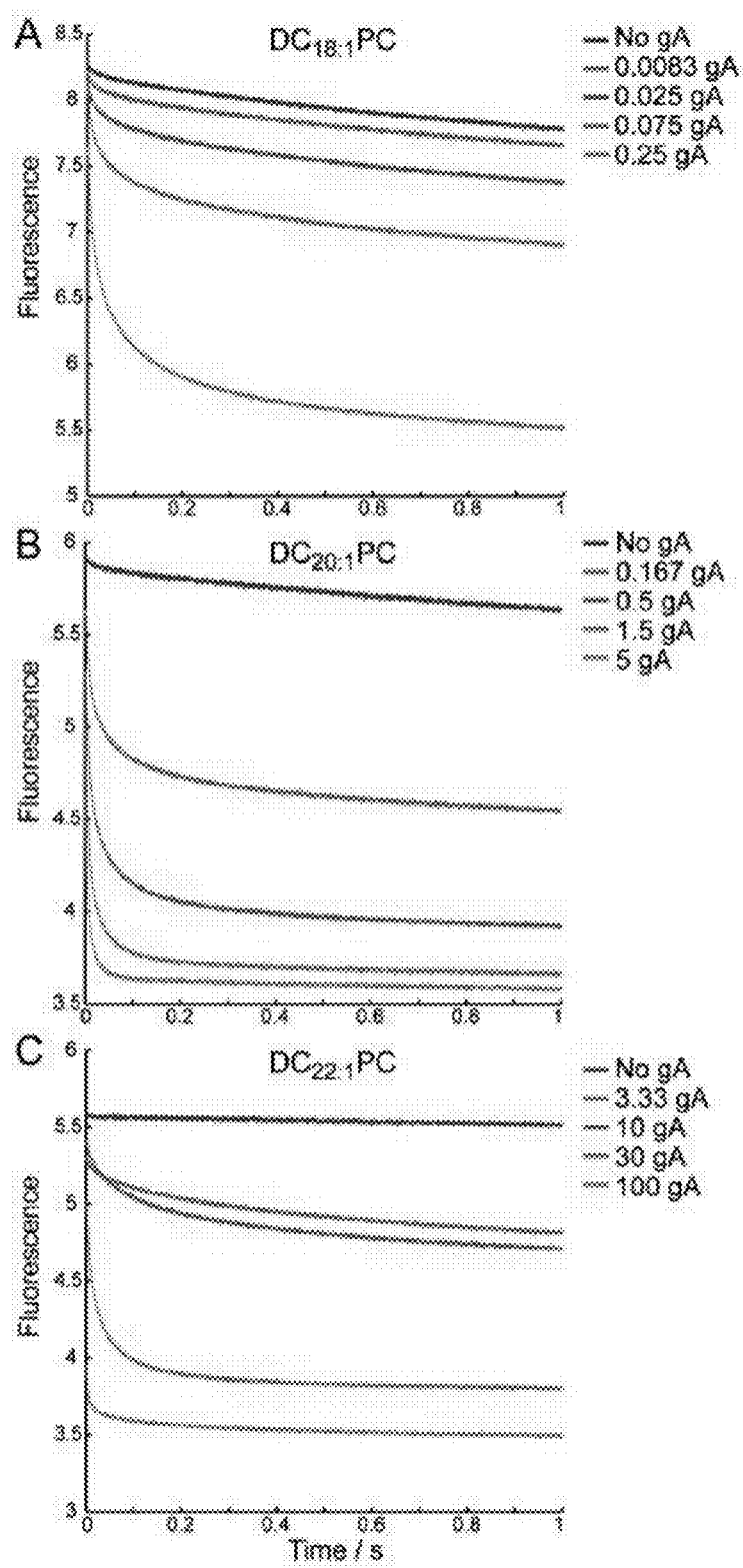
FIG. 9. Time course of ANTS fluorescence quenching with different amounts of gA. A), B) and C) show results with LUV vesicle populations made from $DC_{18:1}PC$, $DC_{20:1}PC$ and $DC_{22:1}PC$, respectively. Notice the different amounts of gA added for the different vesicle populations, the numbers represent the amount of gA added, as µL of a 50 ng per mL gA stock solution.

In some embodiments, $DC_{18:1}PC$ lipids, $DC_{20:1}PC$ lipids, $DC_{22:1}PC$ lipids, or combinations of these lipids, are used in forming the vesicles. As shown in FIG. 9, the $Tl^+$ permeability across the lipid membrane formed with each of these lipids (and in the absence of gA) is slow enough at the relevant time scale (100 ms) that the total amplitude, even for the shortest lipids ($DC_{18:1}PC$), did not amount to a significant portion of the total signal.

In other embodiments, $DC_{20:1}PC$ lipids, $DC_{22:1}PC$ and combinations of the two lipids, are used to form lipid vesicles, which permits the use of native gramicidin from *Bacillus brevis* to achieve effective detection of changes in the monomer⇌dimer equilibrium. Native gramicidin from *Bacillus brevis* can be acquired from Sigma-Aldrich®, among other vendors. The native gramicidin from *Bacillus brevis* is mostly composed of (~80%) [Val$^1$]gA (the wild type linear gramicidin, a 15 amino acid long polypeptide) which forms dimers readily in thin bilayers, therefore thicker bilayers are used in order to shift the monomer⇌dimer equilibrium in favor of the non-conducting state.

Figure 3:
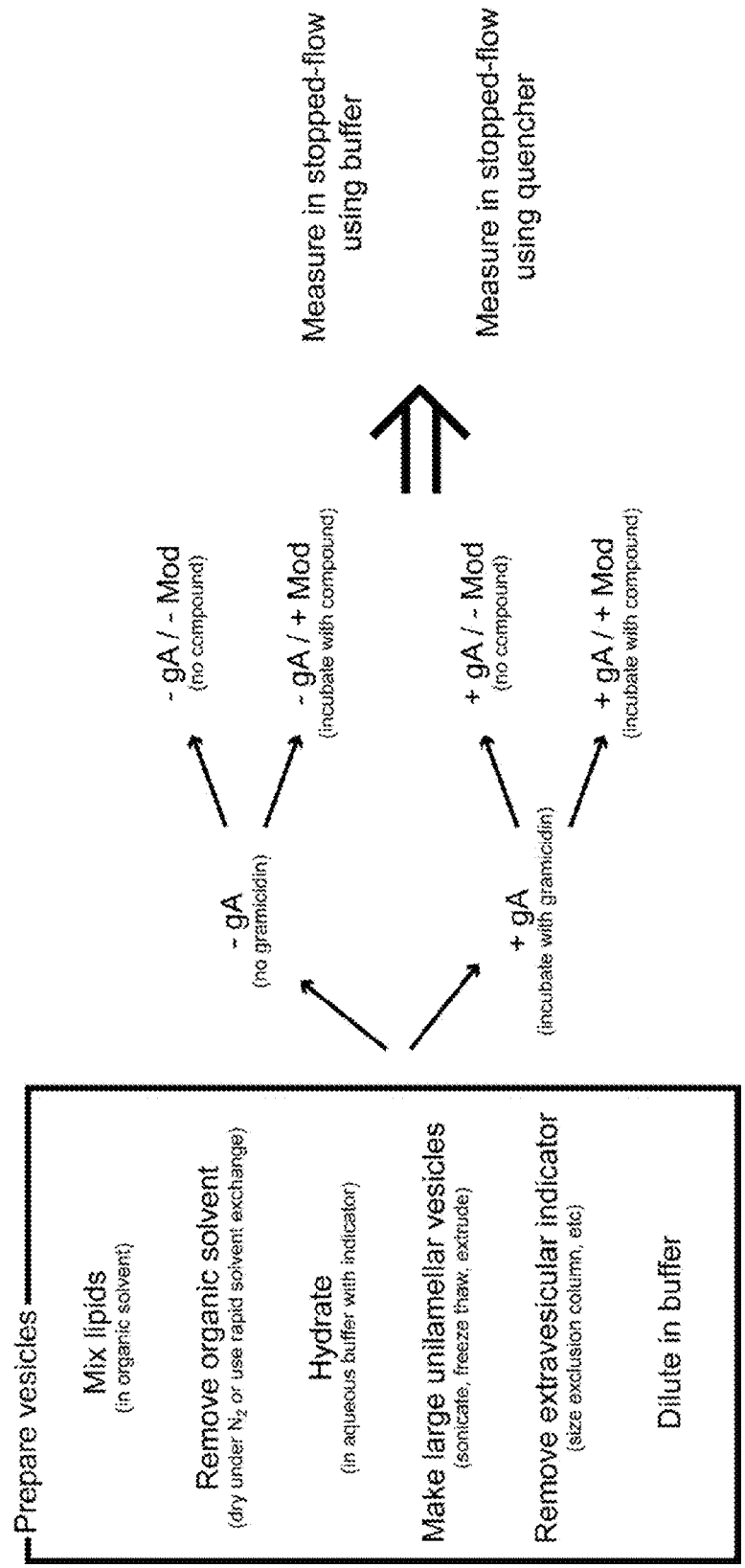
FIG. 3. Flow chart of a high-throughput screening method.
Figure 4:
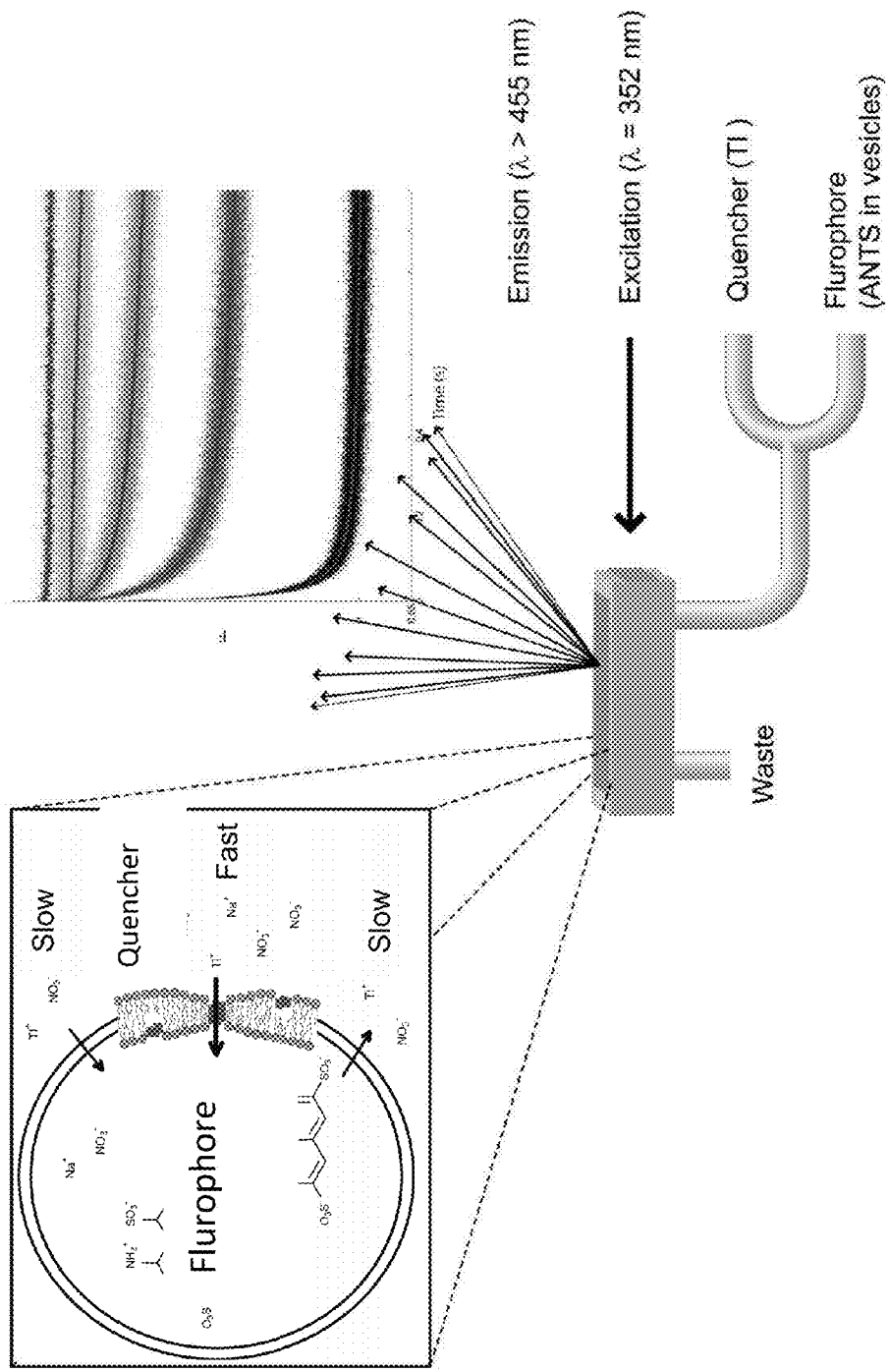
FIG. 4. Schematic diagram showing the stopped-flow mixing cell (bottom). A zoom-in on a single lipid vesicle (top, left), with ANTS and $NaNO_3$ on the inside and $NaNO_3$ and $TlNO_3$ on the outside. The fluorescence signal with time (top, right) of ANTS-filled vesicles without quencher, with quencher, with quencher and pre-doped with 87, 260 and 780 nM gramicidin, in order from top to bottom.

In one embodiment, lipid vesicles loaded or filled with an indicator can be formed by coupling the indicator to the vesicle-forming lipids, or rehydrating dried lipid film in a solution containing the indicator. In an alternative embodiment, lipid vesicles filled with a monovalent cation can be formed by rehydrating dried lipid film in a solution containing the cation. In either embodiment, the suspension of filled vesicles is then sonicated and subjected to 5-6 freeze thaw cycles to form vesicles. The resulting suspension is extruded a number of times using a mini-extruder and a polycarbonate membrane filter of a pore size (e.g., 0.1 μm) to form vesicles of a relatively uniform diameter. By relatively uniform diameter, it is meant that the diameters of the vesicles follow a Bell shaped distribution, with a standard deviation that is about 35%, 30%, 25% or lower, from the mean value. For example, in some embodiments, the vesicles have a mean diameter of 150 nm, and a standard deviation of 50 nm. Indicator or cation material that is external to the vesicles can be removed by filtering though a size exclusion column, for example. A diagrammatic overview of this process is depicted in FIG. 3.

For vesicles to be doped with gramicidins, specific examples of gramicidins that can be used include native gramicidins isolated from *Bacillus brevis*, available from Sigma-Aldrich®, as well as various gA analogues such as the amino acid sequence-shortened analogue des-Val$^1$-Gly$^2$-gramicidin A, the sequence-extended analogue [Ala$^{0a}$, D-Ala$^{0b}$]gramicidin A, and analogues such as [Ala$^1$]gA and [D-Ala$^2$]gA that have reduced and increased single-channel lifetimes, respectively, relative to the native [Val$^1$]Ga, the native [Val$^1$]Ga having the sequence formyl-L-Val-Gly-L-Ala-D-Leu-L-Ala-D-Val-L-Val-D-Val-L-Trp-D-Leu-L-Trp-D-Leu-L-Trp-D-Leu-L-Trp-ethanolamine (SEQ ID NO: 1), as described by Urry in *Proc. Nall. Acad. Sci. USA* 68:672-6 (1971), the content of which is incorporated herein by reference.

Assay Procedure And Signal Processing

In one embodiment, large unilamellar vesicles (LUVs), an indicator-monovalent cation pair, and a preparation of gramicidins are provided for measuring the effects of a test compound on the lipid bilayer.

In a specific embodiment of the invention, the indicator is the cation-sensitive fluorophore, 8-aminonaphthalene-1,3,6-trisulfonic acid disodium salt (ANTS), which can be purchased from Invitrogen, Molecular Probes (Eugene, Oreg.); and the monovalent cation is $Tl^+$.

In one embodiment, at least a portion (i.e., a subpopulation) of the LUVs have been loaded with one member of the indicator-monovalent cation pair, while another portion of the LUVs are not loaded and are used as control. In one specific embodiment, the LUVs have been filled with an indicator such as a fluorophore (e.g., ANTS).

The LUVs are then doped with gramicidin, and undoped LUVs are used as control. In order to incorporate gramicidin molecules into the bilayer of the LUVs, the LUVs are incubated with a desired amount of gramicidin, typically provided in a suitable solution (e.g., DMSO or ethanol). By "doped" is meant herein that gramicidin molecules have been introduced and incorporated into the lipid bilayer of vesicles. The doping process is further described in Example 1 below. The incubation of the LUVs and the gramicidin is conducted for sufficient time to achieve adsorption equilibrium to both sides of the LUVs bilayer (and for the gA monomer⇌dimer equilibrium to be established). The amount of gramicidin used in the incubation is chosen such as to establish an initial monomer⇌dimer equilibrium, which allows for changes in the equilibrium caused by a test compound to be effectively detected and reproducibly correlated with the changes in the detectable signals generated. For any given type of gramicidin molecule or analogue, different concentrations of gramicidin can be tested and compared, as illustrated in Example 3 and FIG. 5, and a desirable concentration can be selected that provides the most effective detection.

Afterwards the vesicles are exposed to a solution containing the other member of the indicator-monovalent cation pair that is not loaded into the vesicles. Upon movement of the cation across the vesicle membrane (through conducting gA channels), the indicator generates a detectable signal. When ANTS/$Tl^+$ are used as a pair of indicator/monovalent cation, the ANTS fluorescence is quenched by the heavy cation $Tl^+$, which can permeate conducting gA channels. In this case, the "detectable signal" is the loss or quenching of the fluorescent signal of ANTS.

In one embodiment, the LUVs are loaded with ANTS. Thus, when ANTS-loaded LUVs and a Tr-containing solution are mixed in a stopped-flow spectrofluorometer, the fluorescence decays in response to increased intravesicular quencher concentration, which is determined by the rate of quencher influx. The quencher, $Tl^+$, permeates the vesicles lipid bilayer slowly but passes readily through conducting (bilayer-spanning) gA channels. The rate of fluorescence quenching (i.e., loss of fluorescence signal over time) is therefore proportional to the gA channel activity (time-averaged number of conducting channels in the membrane).

Figure 5:
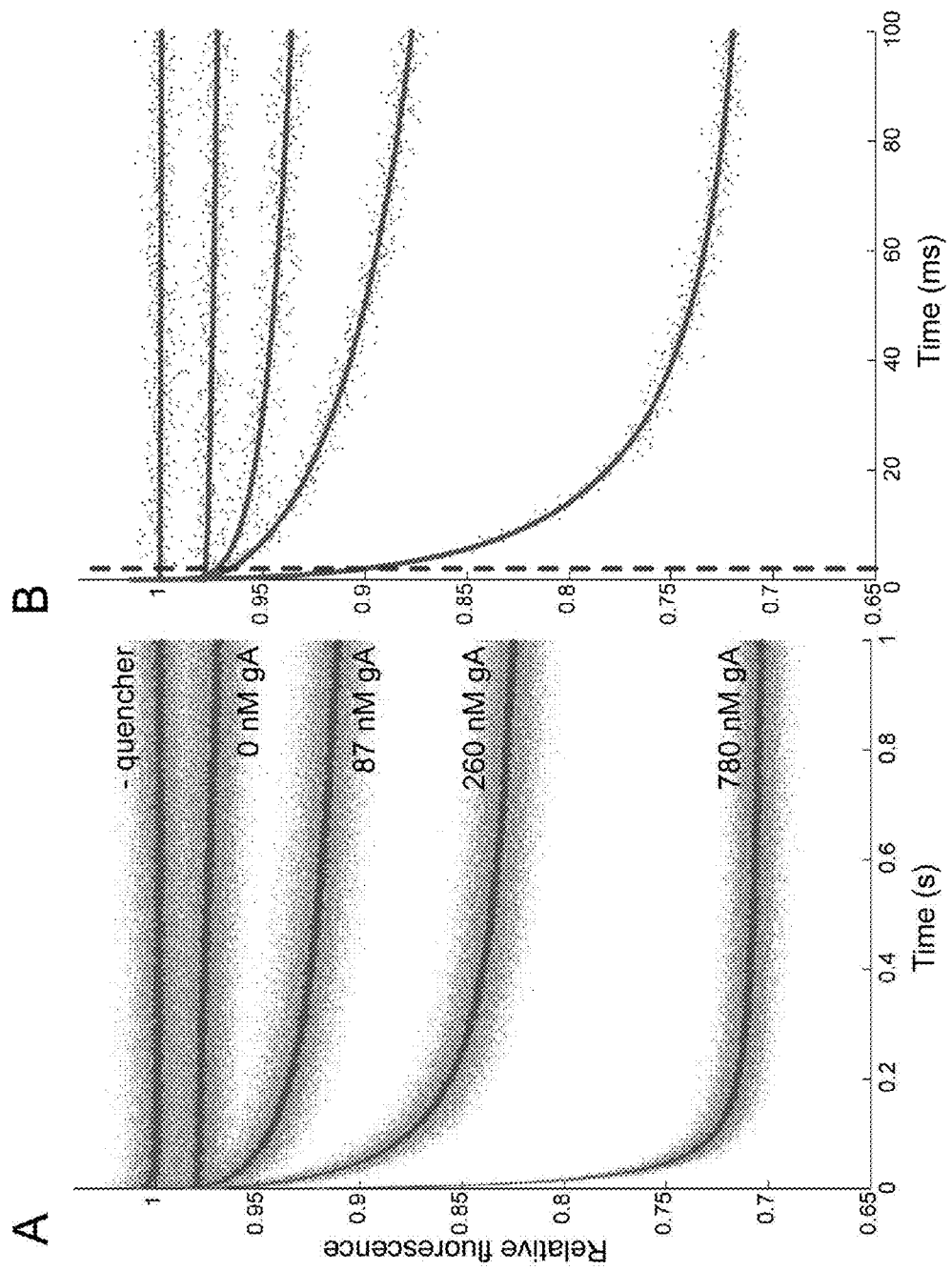
FIG. 5. Fluorescence quenching in the absence and presence of gA. Relative fluorescence signal obtained with ANTS-filled vesicles shown (from top to bottom): without quencher, with quencher, and with quencher and doped with 87, 260 and 780 nM gA. A) 1 s traces; dots denote results from all individual repeats (n>5 per condition); solid lines within dots denote the average of all repeats. B) 100 ms traces; dots are from an individual repeat; solid lines within dots are stretched exponential fits (2-100 ms) to those repeats. The stippled vertical line denotes the 2 ms mark, which is the instrumental dead time.

FIG. 5 further illustrates this embodiment of the invention. In the absence of quencher, the ANTS-filled LUVs fluoresce steadily without photo-bleaching over the relevant time scale. This can be seen as the top curve in FIG. 5A. In the presence of Tl$^+$, but without any gramicidin (FIG. 5A, second from the top curve), there is a small instantaneous drop in fluorescence due to the quenching of extravesicular ANTS and slow reduction in fluorescence due to leakage of Tl$^+$ across the vesicle membrane. Doping the vesicles with increasing amounts of gramicidin (FIG. 5A curves three to five from the top) causes an increase in the rate of fluorescence decay due to Tl$^+$ influx through higher numbers of conducting gA channels. FIG. 5B shows the fitting of a stretched exponential to the first 2-100 ms of to the influx rate data.

To measure the effects of a test compound on the lipid bilayer, the LUVs loaded with one member of the indicator-cation pair, either doped or undoped with gramicidin, are incubated with the test compound for sufficient time to achieve adsorption equilibrium and for the gA monomer-dimer equilibrium to be established after the lipid bilayer properties have been modified by the test compound. A portion of the LUVs is exposed to the solvent used to dissolve the compounds, but without the test compound, for use as control.

After exposing the lipid vesicles to the test compound, the vesicles are exposed to a solution containing the other member of the indicator-cation pair. Fluorescence quenching (i.e., loss of fluorescence signal) over time is measured, and the measurements from LUVs treated with a test compound are compared to the measurements from LUVs without a test compound in order to determine whether the test compound has any bilayer-modifying effect.

Figure 6:
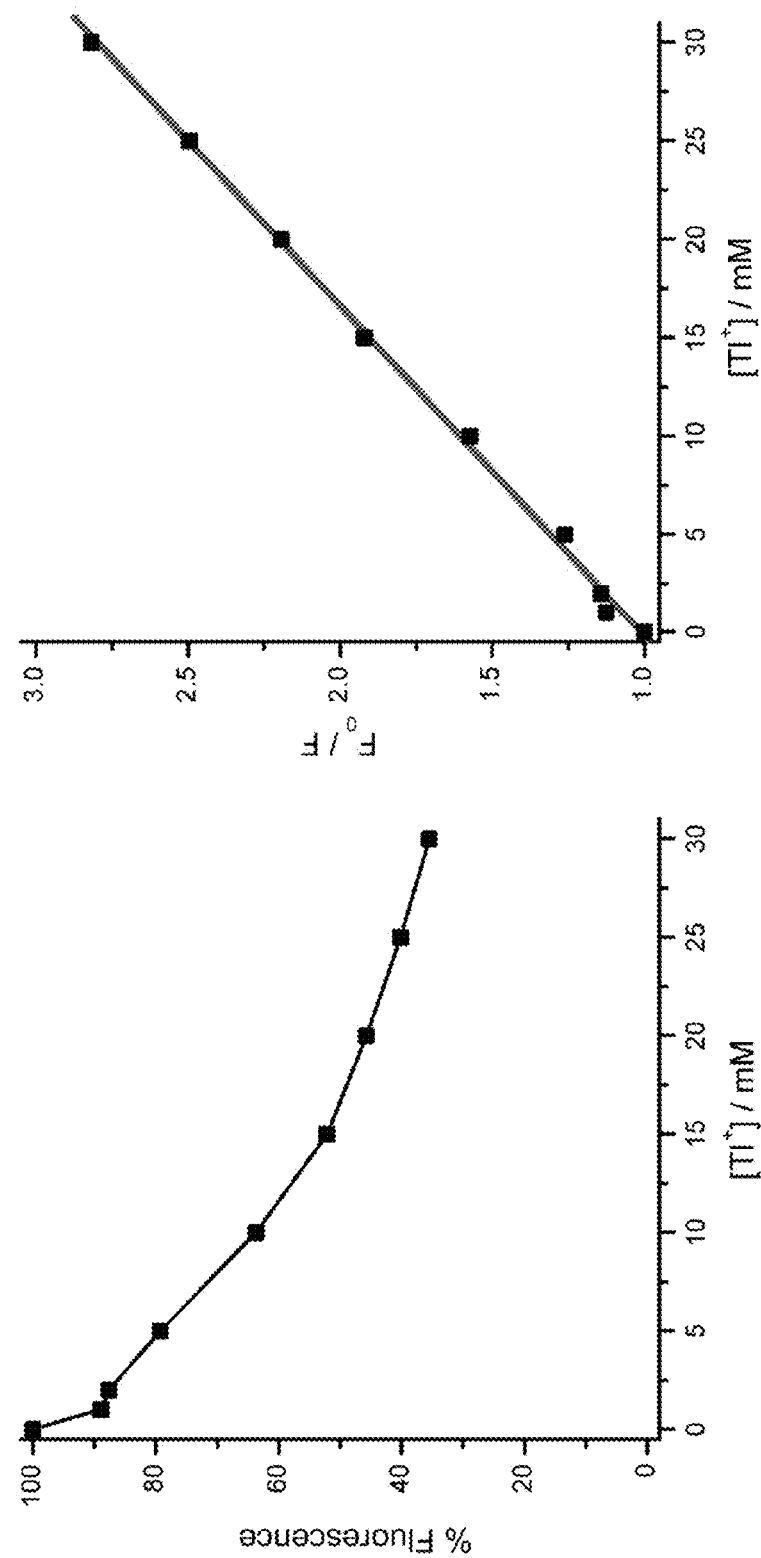
FIG. 6. Determination of the Stern-Volmer quenching constant (K), see Example 8, was determined by fitting a straight line to $F_0/F$ vs. $[Tl^+]$, using 200 µM ANTS in the presence and absence of 0-30 mM $TlNO_3$ and an electrolyte solution with fixed ionic strength of 150 mM, maintained by varying amounts of $NaNO_3$, 10 mM HEPES buffered at pH 7.0.

In order to make such determination, measurements from the assay (e.g., fluorescence quenching over time) are processed and converted to a value which can be used as basis of comparison. First, in embodiments where a fluorescent indicator is quenched by cation, the quenching constant is determined for a given electrolyte solution (and ionic strength) and fluorophore/quencher pair, as illustrated in Example 6. The quenching constant (K) is a measure of the effectiveness of quenching, and is used in the Stern-Volmer equation:

$$\frac{F_0}{F} = 1 + K[Q], \tag{1}$$

where $F_0$ and $F$ are the fluorescence intensity in the absence and presence of the quencher and [Q] is the concentration of the quencher. The quenching constant should be known so that the quencher concentration can be chosen such that that the quenching varies as an approximately linear function of the quencher concentration, see e.g. FIG. 6 for ANTS and Tl$^+$.

Next, the measured signal is correlated to an intermediary value that can be used as surrogate that reflects changes to the lipid bilayer. For example, the measured signal—fluorescence decay—is correlated to the speed of quencher influx, which in turn indicates the number of conducting gA channels; and therefore changes in the measured signal are indicative of changes in the formation frequency and lifetime of the vesicle-incorporated gramicidin channels as a result of changes in the lipid bilayer properties caused by the test compound.

Several factors are considered in this correlative analysis. In a commercially relevant experimental setting, vesicles vary in size. In experiments in which quencher and indicator are used, quenchers can enter vesicles in at least two ways—through open channels at very fast influx rates, and by diffusion through the membrane itself at generally much slower influx rates.

As a result of these complexities, both the simplest single-exponential mathematical model for quencher influx, as well as more developed double- or multi-exponential models, give low signal/noise ratios, as shown in Examples 4 and 5.

The inventors have determined that for short time intervals a stretched exponential, Eq. 2, cf. (Berberan-Santos et al., Chem. Physics 315:171-182 (2005)) fits all influx rates without over-fitting:

$$F(t)=(F(0)-F(\infty))\cdot\exp\{-(t/\tau_0)^\beta\}+F(\infty) \tag{2}$$

where F(t) is the fluorescence as a function of time t, F(0) and F(∞) the fluorescence at t=0 and t→∞, β is a parameter that depends on the dispersity of the LUVs (0<β≤1) and $\tau_0$ a parameter with units of time. Both β and $\tau_0$ are determined based on this data.

However, a stretched exponential analysis is complicated because a key variable, the initial rate of decay at time=0, is indefinite. The inventors have made a further determination that a reproducible measure of changes in fluorescence time course is the estimated quenching rate at a given time (after the fluorophore-loaded LUVs are mixed with the quencher solution), where the rate is defined as $$k(t)=(\beta/\tau_0)\cdot(t/\tau_0)^{(\beta-1)} \tag{3}$$

For the ANTS/Tl$^+$ fluorophore quencher pair, it has been determined that the most reproducible measure of changes in fluorescence time course is the estimated quenching rate (eq. 3) at 2 ms.

It is thus possible to determine how different drugs and other bilayer-perturbing compounds alter the rate of changes in measured signals (e.g., rate of fluorescence quenching) and thereby obtain a measure of the changes in the number of conducting gA channels, which in turn provides for a measure of the changes in the bilayer deformation associated with gA channel formation.

A compound is considered to significantly alter the bilayer or has a significant bilayer-modifying effect if at a given concentration, the compound significantly changes the rate of the signal being generated because of the increased movement of the monovalent cation across the vesicle membrane (e.g., the rate of fluorescence quenching). A change is considered significant if the rate has been increased or decreased by at least about 20%.

As described above, in some embodiments, a subpopulation of the LUVs have been loaded with the indicator of the indicator-cation pair. The vesicles are doped with gramicidin and treated with a test compound, and then exposed to an extravesicular solution which contains the cation of the indicator-cation pair, wherein movement of the cation across the lipid bilayer through a conducting gramicidin channel into the vesicles causes the indicator to generate a detectable signal.

In other embodiments of the invention, a subpopulation of the LUVs have been loaded with the indicator-cation pair. In these embodiments, the vesicles are doped with gramicidin, treated with a test compound, and then exposed to an extravesicular solution which does not contain the cation, wherein movement of the cation across the lipid bilayer through a conducting gramicidin channel out of the vesicles causes the indicator to generate a detectable signal.

Therefore, one can generate a signal (increased or decreased fluorescence/absorbance) either by putting the indicator and cation in contact with each other, or by separating the indicator and cation, which would produce a signal of the opposite sign.

Automated Assay

Figure 10:
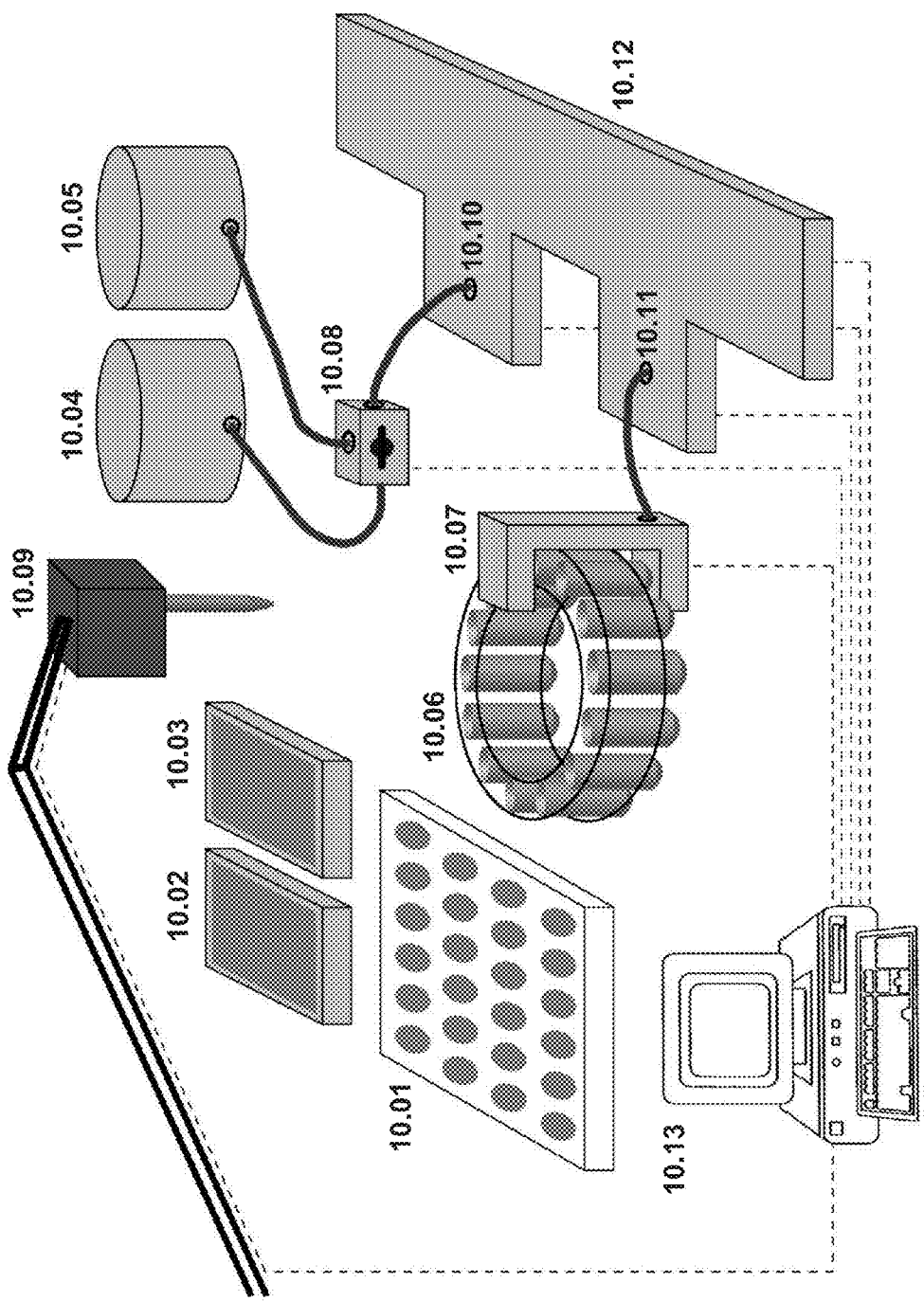
FIG. 10. Schematic of a robotic implementation of the device.

The assay of the present invention can be practiced by a human user, or it can be practiced by an automated robotic system. To illustrate, one embodiment of an automated robotic system is depicted in FIG. 10 and further described below.

The automated robotic system includes a multi-well tray containing test compounds and controls (10.01).

The robotic system also includes a container with gramicidin-doped LUVs (10.02), and a container with LUVs without gramicidin (10.03) for use as a control. These LUVs are loaded with an indicator. In an alternative embodiment, these LUVs can be loaded with cations, and the indicator will be provided in a solution in 10.04. For optimal liposome stability, the container should be temperature-controlled with the temperature maintained slightly above the liposome phase transition temperature.

The robotic system additionally includes a container with a solution comprising gramicidin channel permeable cations that interact with the indicator (10.04). In the alternative embodiment where LUVs are loaded with cations, the indicator solution is provided in the container 10.04.

The LUVs are mixed with test compound or control. The mixing may take place in a single-well device, or in a device that has multiple wells in any configuration. In the embodiment shown in FIG. 10, the device has multiple wells (10.06). Any such single-well or multiple-well device may be incorporated into the rapid mixing and recording system. For consistency among experiments and the ability to incubate at different temperatures, temperature control could be added to these containers (10.06).

To place a desired amount of a LUV-containing solution into the mixing well in 10.06, a robotic pipetter may be used, as shown in FIG. 10 as 10.09. The robotic pipetter may be the same as the one that will be subsequently used to fetch test or control solutions as in FIG. 10, or it may by different. Separate robotic pipetters may be used to pipette gramicidin-doped LUVs and non-gramicidin-doped LUVs, or as shown in FIG. 10, the same robotic pipetter may be used. Alternatively, lines may run from each container of LUV solution to the mixing well in 10.06, and the relevant LUV solution may be pumped into the mixing well under automated control.

To place a desired amount of solution containing a test compound or a control into the mixing well in 10.06, a robotic pipetter (10.09) may again be used, as shown in FIG. 10. The robotic pipetter used for this purpose may have a single pipette channel, as shown in FIG. 10, or may have multiple channels.

Prior to the next step, the LUVs are incubated with a test chemical or control for sufficient time to achieve adsorption equilibrium and for the gA monomer-dimer equilibrium to be established, e.g., for approximately 10 minutes. During the incubation period the device may be engaged in mixing LUVs and test chemicals or controls in other mixing wells, and may be engaged in other maintenance tasks, for example and without limitation, changing disposable pipette tips or flushing the rapid mixing and recording system.

Once the incubation/equilibration is complete, the solution in the mixing well is pumped or allowed to flow by a device (10.07) under computer control into the injector (10.11). Alternatively the solution may be pumped directly into the rapid mixing and recording system (10.12).

The system loads solution from the container with a solution comprising cations (10.04) or from the container containing control solution (10.05), under control of a three-way valve 10.08, into the injector (10.10). Alternatively, the desired solution may be loaded directly into the rapid mixing and recording system (10.12).

Under control by a suitably programmed computer, the injectors 10.10 and 10.11 are activated, the solutions mix, and the reaction is recorded in the rapid mixing and recording system (10.12), which may be a stopped-flow spectrofluorometer. The injectors may be activated sequentially or simultaneously, if needed to determine the time course of the changes in bilayer properties. Alternatively, if solutions are injected directly from the mixing well (10.06) into the rapid mixing and recording system (10.12) and/or from the cation or control containers (10.04 and/or 10.05), the injections may occur sequentially or simultaneously. The system may include multiple instances of the rapid mixing and recording system (10.12). The rapid mixing and recording system (10.10, 10.11 and 10.12) can be flushed between samples by loading every other container in 10.06 with buffer or other solvents and injecting buffer (or connecting a additional container with other solvents) from 10.08.

After loading all the samples onto 10.01-10.05, a suitable computer 10.13 can be programmed to operate the robotic system fully automatically. The results from the rapid mixing and recording system (10.12) are transferred to computer (10.13) as shown in FIG. 10. The results may be fluorescence quench time courses, or other measurements as described above. The computer may be the same device that controls the rest of the system as in FIG. 10, or it may be a separate computer.

The computer executes the algorithm described above and displays the results. The analysis computer may also alert the user to the important, results statistically deviating from control, (as well as the technically problematic) results. For example, when the individual results from different measurements with the same compound are analyzed, the results are inspected (by the computer) for consistency. If the variation of the results from analysis is beyond a threshold value, the computer could eliminate an outlier based on the calculated mean and standard deviation. After eliminating an outlier from the analysis, the consistency check could be repeated before completing the analysis for that compound.

In the following examples, specific embodiments of the invention are illustrated and reference is made to the accompanying drawings. These embodiments are described in detail to enable those skilled in the art to practice the invention, and it is to be understood that other embodiments may be utilized and that changes may be made without departing from the scope of the present invention. The following description of exemplary embodiments is, therefore, not to be taken in a limited sense.

EXAMPLE 1

Detailed Protocols

Chemicals:

| | |
|---|---|
| $DC_{18:1}PC$ | 1,2-Dioleoyl-sn-Glycero-3-Phosphocholine (MW = 786.15 g/mol). |
| $DC_{20:1}PC$ | 1,2-Dieicosenoyl-sn-Glycero-3-Phosphocholine (MW = 841.656 g/mol). |
| $DC_{22:1}PC$ | 1,2-Dierucoyl-sn-Glycero-3-Phosphocholine (MW = 898.34 g/mol). |
| ANTS | 8-aminonaphthalene-1,3,6-trisulfonic acid, disodium salt (MW = 427.33 g/mol). |

-continued

| | |
|---|---|
| DMSO | Dimethylsulfoxide (MW = 78.13 g/mol). |
| TlNO$_3$ | Thallium nitrate (MW = 266.39 g/mol). |
| NaNO$_3$ | Sodium nitrate (MW = 84.99 g/mol). |
| HEPES | 4-(2-Hydroxyethyl)piperazine-1-ethanesulfonic acid (MW = 238.30 g/mol). |
| gA | Gramicidin from *Bacillus aneurinolyticus* (*Bacillus brevis*) (MW ≈ 1900 g/mol). |

Equipment:

SX.20 stopped-flow fluorescence spectrophotometer from Applied Photophysics Limited (Leatherhead, UK).

Mini-Extruder, with 0.1 μm filters, from Avanti Polar Lipids (Alabaster, Ala.).

Data analysis performed in MATLAB 7 from The Math-Works, Inc (Natick, Mass.).

PD-10 Desalting column, Sephadex G-25 medium for a matrix, from GE Healthcare (Piscataway, N.J.).

Stock Solutions:

| | |
|---|---|
| S_ANTS | 75 mM ANTS at pH 7.0 in water. |
| S_Na_Filling | 150 mM NaNO$_3$ 15 mM HEPES at pH 7.0 in water. |
| S_Na_Buffer | 140 mM NaNO$_3$ 10 mM HEPES at pH 7.0 in water. |
| S_Tl_Quencher | 50 mM TlNO$_3$ 94 mM NaNO$_3$ 10 mM HEPES at pH 7.0 in water. |

For all stock solutions, pH was adjusted using HNO$_3$ or NaOH.

Generation of ANTS-Filled Liposomes:

Day 1:
1. Remove lipid from freezer and let it equilibrate to room temperature.
2. Add 0.6 mL of lipid of 25 mg/mL solution in chloroform to a 25 mL round bottom flask.
3. Continually rotate flask while drying under nitrogen, until all the chloroform has evaporated and a thin film of lipid coats the entire lower half of the flask.
4. Dry further in dessicator under vacuum overnight.

Day 2-3:
1. Rehydrate in 100 mM NaNO$_3$, 25 mM ANTS (Na salt), 0 mM HEPES at pH 7.0. (⅓ S_ANTS and ⅔ S_Na_Filling, gives a total of 150 mM Na$^+$) use 1.905 mL for DC$_{18:1}$PC, 1.785 mL for DC$_{20:1}$PC, and 1.671 mL for DC$_{22:1}$PC to get a 10 mM lipid concentration, vortex thoroughly.
2. Age at room temperature 3-4 hours (or over night), keep away from light.
3. Sonicate lightly (1 min in a low power sonicator).
4. Freeze-thaw solution 5-6 times.
5. Extrude though a 0.1 μm filter 21 times. Clean extrusion equipment with water and 2-Probanol.
6. Filter out external ANTS by running through a PD-10 Desalting column with 140 mM NaNO$_3$, 10 mM HEPES, pH 7.0 elution buffer. Clean column with buffer, add 1.5 mL of 10 mM sample+1 mL buffer. Now collect sample eluting with 3 mL buffer, resulting solution should contain around 4-5 mM lipids.
7. If not used directly store in refrigerator, shielded from light for maximum of 7 days. Do not freeze lipids, as that will cause a breakdown of their barrier properties. The freeze point can be well above 0° C.; in the case of DC$_{22:1}$PC it is 11° C.

Mixing Fluorescence Solution:

24 hours before fluorescence measurements, ANTS-filled liposomes were mixed 1:20 in S_Na_Buffer. For the portion of liposomes that are to be doped with gramicidin, the desired amount of gramicidins was added at this time. 24 hours was shown to be sufficient to equilibrate the gramicidin between the lipid vesicles inner and outer monolayers. Gramicidin diluted in DMSO was used, but the added DMSO was kept to an absolute minimum (<0.1% of volume) as DMSO of >0.5% affects bilayer properties. The solution was stored at 12-13° C. in the dark.

Suggested gramicidin concentrations:

| | | | |
|---|---|---|---|
| DC$_{18:1}$PC | 0.65 nM | 0.25 μL, of | 5 μg/mL gramicidin |
| DC$_{20:1}$PC | 2.6 nM | 1 μL, of | 5 μg/mL gramicidin |
| DC$_{22:1}$PC | 260 nM | 1 μL, of | 500 μg/mL gramicidin |

Fluorescence Measurements:

The Applied Photophysics SX.20 stopped-flow fluorescence spectrophotometer was used for the measurements. The Xenon lamp generally takes up to 45 min to reach optimal performance and the water bath took a similar time to reach the desired temperature.

Recommended settings were:
slit width 1/1,
λ=455 nm high pass filter in detector 1,
120 μL volume (dead time should be≈1.2 ms),
water bath set at 25° C.,
excitation λ=352 nm,
detection high voltage around 422 V,
sample 5000 points (linear) for 1 second,
use "pressure hold on".

The modifier in question was diluted in DMSO. The same amount of DMSO was added to all samples, including control. The concentrations were adjusted for the particular vesicle lipid composition (in the case of gramicidin) and compound to be tested (as they may have different potencies).

Suggested sequence for a standard modifier; use six different conditions:

| | | |
|---|---|---|
| 1. | no gramicidin, | 0 μM modifier |
| 2. | no gramicidin, | 100 μM modifier |
| | | (the max modifier concentration) |
| 3. | with gramicidin, | 0 μM modifier |
| 4. | with gramicidin, | 1 μM modifier |
| 5. | with gramicidin, | 10 μM modifier |
| 6. | with gramicidin, | 100 μM modifier |

For each condition:
1. Use 1.5 mL of diluted ANTS-liposomes for each condition (compound, concentration).
2. Add compound at the desired concentration and incubate for 10 min at 25° C. (keep in dark), or DMSO for controls.
3. Record fluorescence, x8 repeats, with S_Na_Buffer (the first four should be removed due to mixing).
4. Record fluorescence, x12 repeats, with S_Tl_Quencher (the first four should also be removed due to mixing).

EXAMPLE 2

Materials and Methods

This Example describes the materials and methods used in Examples 3-8 except as otherwise indicated.

Generate fluorescent liposomes. The fluorophore 8-aminonaphthalene-1,3,6-trisulfonic acid disodium salt (ANTS), Invitrogen, Molecular Probes (Eugene, Oreg.), was loaded into large unilamellar vesicles (LUVs) using hydration mini-extrusion (Hope et al., *Biochim. Biophys. Acta* 812:55-62 (1985)) as follows. 1,2-Dierucoyl-sn-Glycero-3-Phosphocholine lipids, from Avanti Polar Lipids (Alabaster, Ala.), were bought in a lipid/chloroform solution and used without further purification. For each batch of vesicles, the lipid/chloroform solution was dried under nitrogen and then further dried in a dessicator under vacuum overnight to fully remove the chloroform. The dried lipid film was rehydrated in 100 mM $NaNO_3$, 25 mM ANTS, 10 mM HEPES at pH 7.0 at room temperature over night, volume was adjusted to give a 10 mM lipid concentration. The suspension was then sonicated in a low power sonicator for 1 min, subjected to 5-6 freeze thaw cycles and extruded 21 times, at room temperature, using Avanti mini-extruder, Avanti Polar Lipids (Alabaster, Ala.), and a 0.1 μm Polycarbonate Membrane filter. External ANTS was removed by filtering though a PD-10 Desalting column, GE Healthcare (Piscataway, N.J.). Prepared ANTS-LUV stock was stored at 12-13° C. in the dark for a maximum of seven days. Before the fluorescence experiments ANTS-LUV stock was diluted 1:20 with 140 mM $NaNO_3$, 10 mM HEPES, pH 7.0 buffer. For the portion of vesicles to be doped with gA the desired amount of gramicidin from *Bacillus aneurinolyticus*, Sigma Chemical Co. (St. Louis, Mo.), diluted in dimethylsulfoxide (DMSO) was added and incubated for 24 hours at 12-13° C. in the dark.

Incubating the LUVs with the Compounds to be Tested.

The compounds were incubated with the ANTS-LUV solution, at the test temperature in the dark, for sufficient time to achieve adsorption equilibrium (and for the gA monomer⇌dimer equilibrium to be established after the lipid bilayer properties have been modified) 10 min, at 25° C. in the dark. The final DMSO concentrations were kept consistent for all samples and under 0.5% with the exception of when DMSO was tested, then listed amounts where used and no DMSO was added to controls.

Fluorescence Spectrofluorometry.

The fluorescence was measured using a SX.20 Stopped-Flow Spectrometer (Applied Physics, Leatherhead, UK), with a 150-W Xenon lamp, a two sample rapid mixing unit with machine dead time~1.2 ms and a thermostatting water bath set to 25° C. The samples were excited at X=352 nm and fluorescence was recorded though λ=455 nm high pass filter with Pro-Data control software from Applied Photophysics, sampling 5000 points a second. For each sample at least 10 repeated mixing trials were measured, from two or more vesicle preparations. Each repeat was separately analyzed using MATLAB v7.4, The MathWorks, Inc (Natick, Mass.). The time course of fluorescence quenching was normalized to the average fluorescence without quencher, for that particular sample, and the first 2-100 ms of the time course was fitted with a stretched exponential. The initial influx rate is quantified as the rate of the stretched exponential at 2 ms.

EXAMPLE 3

Fluorescence Quenching Depends on Gramicidin Activity

Gramicidin A (gA) channel activity was measured by monitoring the rapid loss of fluorescence signal over time. The fluorescence decayed in response to increased intravesicular quencher concentration, which is determined by the rate of quencher influx (See FIG. 2). The quencher, $Tl^+$, permeates the vesicles lipid bilayer slowly (Gutknecht, *Biochim. Biophys. Acta* 735:185-8 (1983)) but passes readily through conducting (bilayer-spanning) gA channels (Neher, *Biochim. Biophys. Acta* 401:540-544 (1975); Andersen, In: *Renal Function*. 71-99 (1978)). The rate of fluorescence quenching is therefore proportional to the gA channel activity (time-averaged number of conducting channels in the membrane).

In the absence of quencher, the ANTS-filled LUVs were seen to fluoresce steadily without photo-bleaching over the relevant time scale (FIG. 5A top curve). In the presence of $Tl^+$ (FIG. 5A second curve from the top) there was a small instantaneous drop in fluorescence due to the quenching of extravesicular ANTS. There was also a slow fluorescence decay due to leakage of Tr across the vesicles membrane. Doping the vesicles with increasing amounts of gA (FIG. 5A curves three to five, from top 87, 260 and 780 nM gA, respectively) caused an increase in the rate of fluorescence decay due to Tr influx through higher numbers of conducting gA channels. FIG. 5B shows the quantification of the influx rate using the rate of a stretched exponential. As discussed in Example 4, the time course of fluorescence quenching is better described by a stretched exponential, rather than by a single exponential.

EXAMPLE 4

Analysis of Time Course of Fluorescence Quenching

Theoretically for an enclosed volume of a given size, the $Tl^+$ influx can be described as a first order process:

$$T(t)=T_\infty(1-e^{-kt}) \quad (4)$$

where t is time, k the rate constant of $Tl^+$ influx, T(t) and $T_\infty$ denote the $[Tl^+]$ at time t and infinity (maximum concentration), respectively. Eq. 4 can be rewritten in terms of the changes in fluorescence (F):

$$\frac{F_0}{F} = 1 + KT_\infty(1-e^{-kt}), \quad (5)$$

where $F_0$ and F denote the fluorescence intensity in the absence and presence of $Tl^+$, K the Stern-Volmer quenching constant, and $T_\infty$ the $[Tl^+]$ (50 mM)/2. The Stern-Volmer quenching constant K is determined in a separate experiment before the measurements begin (see Example 6). In theory Eq. 5 can be fit to the fluorescence quench time course, to get estimates of k for different concentrations of the molecule in question. Then k can be plotted as a function of the increasing concentration of the molecule, and the relative effect of the molecule on the gramicidin function can be observed.

For the gramicidin-based fluorescence assay, however, the ideal description given above may not be a good model because the fluorescence quenching deviates from a single exponential. There are two main reasons for this deviation from the ideal single exponential time-course described above. First, the inventors have determined that the vesicles in this assay are not all the same size. From electron microscopy images, when 0.1 μm filter was used to make the vesicles, the vesicle size was determined to be approximately normally distributed with average vesicle diameter around 150 nm and standard deviation of 50 nm. Small vesicles have smaller volume and therefore fill much faster than large vesicles. In addition, the number of gramicidin monomers per vesicle scales with the radius squared, whereas the fluorescence signal and the amount of quencher needed to achieve a given degree of quench scale with the radius cubed. Second, gramicidin channels are permeable to the quencher $Tl^+$, as well as other suitable monovalent ions. Given the small size of the vesicles, vesicles with one or more open gramicidin channel therefore will fill up very fast. That is, at time zero, a fraction of all the vesicles will have one or more open gramicidin channel; those vesicles will fill up in a matter of ms, dependent on vesicle size and number of open channels. When the quencher concentration inside reaches that of the outside, the flurophores in those vesicles have been maximally quenched and this vesicle will not contribute to any further reduction of the total fluorescence signal. The rest of the vesicles will have no open gramicidin channels at time zero, but most will have a significant number of gramicidin monomers and one or more channels may form during the time course of the experiment.

Taken together this gives a complex quenching time course: a fast multi exponential component that depends on the time average number of open gramicidin channels in the vesicles (determined by $K_D$, the gA dimerization coefficient); and a slower multi-exponential component based mostly on the frequency of channel openings ($k_1$); in addition to a very slow time course of quencher leakage through the lipid bilayer and fluorescence bleaching. Indeed the fluorescence quenching, at all influx rates, is well approximated using a double exponential at short time intervals (below one second) and a double exponential plus a slow liner component at higher time intervals (data not shown). The double exponentials are for all except the very highest influx rates over fitting the data and therefore hard to interpret and often magnify any noise in the data. For short time intervals a stretched exponential (Berberan-Santos et al., *Chem. Physics* 315:171-182 (2005)) fits all influx rates without over-fitting, as follows:

$$F(t)=(F(0)-F(\infty))\cdot \exp\{-(t/\tau_0)^\beta\}+F(\infty) \quad (6)$$

where F(t) is the fluorescence as a function of time t, F(0) and F(∞) the fluorescence at t=0 and t→∞, β is a parameter that depends on the dispersity of the LUVs and the stochasticity of gA channel formation (0<β≤1) and $\tau_0$ a parameter with units of time.

The stretched exponential has proven useful for the analysis of time-resolved luminescence spectroscopy results (Berberan-Santos et al., *Chem. Physics* 315:171-182 (2005)), but the analysis is complicated because the initial rate of decay of the stretched exponential, at t=0, is infinite. After exploring the properties of the stretched exponential, the inventors found that the most reproducible measure of changes in fluorescence time course was the rate at 2 ms, where the rate is defined as $$k(t)=(\beta/\tau_0)\cdot(t/\tau_0)^{(\beta-1)}. \quad (7)$$

It is thus possible to explore how different drugs and other bilayer-perturbing compounds alter the rate of fluorescence quenching (Tl$^+$ influx) and thereby obtain a measure of the changes in the number of conducting gA channels, which in turn provides for a measure of the changes in the bilayer deformation associated with gA channel formation.

Alternatively, one could convert the time course of fluorescence quenching to changes in the intravesicular [Tl$^+$], using the Stern-Volmer equation; doing so, however, had little effect on the results.

EXAMPLE 5

Analyze Each Repeat Using MATLAB

For each sample, the max fluorescence was determined as the average initial fluorescence of all repeats from this sample without quencher (buffer only). Before normalization, all repeat/samples were checked for systematic drifts in fluorescence signal. If there is a significant shift in fluorescent signal dependent on compound concentration the compound itself might be fluorescent. Samples with no gA and either no compound or maximum compound concentration should both show similar slow fluorescence quenching, representing the slow leakage of Tl$^+$ (in the form of TlNO$_3$ ion pairs) through the vesicles bilayer. If there is a significant difference between the two samples, the compound in question could be perturbing the vesicles bilayer to such an extent that it becomes increasingly permeable to the quencher—which in itself provides a measure of a non-specific breakdown of the bilayer barrier properties. If the data are "good", the first 2-100 ms of the normalized fluorescent time course is fitted by a stretched exponential (Berberan-Santos et al., *Chem. Physics* 315:171-82 (2005)), which for fitting purposes is expressed as (see also Eqs. 6 and 7):

$$y = y_0 + A \cdot \exp\left\{-\left(\frac{t}{\tau}\right)^\beta\right\} \quad (8)$$

To quantify the rate of fluorescence quenching, one can calculate the rate of the fitted stretch exponential at t=2 ms (Berberan-Santos et al., *Chem. Physics* 315:171-82 (2005)), see Eq. 8:

$$k(t) = \frac{\beta}{\tau}\left(\frac{2}{\tau}\right)^{(\beta-1)}, \quad (9)$$

where τ is in ms.

EXAMPLE 6

Determine the Stern-Volmer Quenching Constant (K)

This experiment only needs to be done once for a given electrolyte solution (and ionic strength) and fluorophore/quencher pair in order to determine the Stern-Volmer quenching constant (K).

The Stern-Volmer quenching constant (K) is a measure of the effectiveness of quenching, and is used in the Stern-Volmer equation:

$$\frac{F_0}{F} = 1 + K[Q], \quad (10)$$

where $F_0$ and F are the fluorescence intensity in the absence and presence of the quencher and [Q] is the concentration of the quencher.

To determine K, the quenching of ANTS under different concentrations of the quencher, Tl$^+$, was determined, using an electrolyte solution that is as similar as possible to the one that is used in the gramicidin-based assay. With increasing concentrations of TlNO$_3$, the NaNO$_3$ concentrations were decreased to maintain constant ionic strength.

These measurements could be done in a conventional spectrofluorometer, such as the Perkin-Elmer 650-40 Spectrofluorometer. For each measurement, a standard 3 mL glass cuvette was used, filled with 200 μM ANTS and 10 mM HEPES buffered 150 mM NaNO$_3$ at pH 7.0. The samples were excited at 352 nm and emission was monitored (max should be around 515 nm). TlNO$_3$ was then added to give the following electrolyte compositions:

| | | |
|---|---|---|
| 0 | 0 mM TlNO$_3$ | 150 mM NaNO$_3$ |
| 1 | 1 mM TlNO$_3$ | 149 mM NaNO$_3$ |
| 2 | 2 mM TlNO$_3$ | 148 mM NaNO$_3$ |
| 2 | 5 mM TlNO$_3$ | 145 mM NaNO$_3$ |
| 3 | 10 mM TlNO$_3$ | 140 mM NaNO$_3$ |
| 4 | 15 mM TlNO$_3$ | 135 mM NaNO$_3$ |
| 5 | 20 mM TlNO$_3$ | 130 mM NaNO$_3$ |
| 6 | 25 mM TlNO$_3$ | 125 mM NaNO$_3$ |
| 7 | 30 mM TlNO$_3$ | 120 mM NaNO$_3$ |

F/F$_0$ was plotted against [Tl$^+$] and a straight line was fit to give K in the units of M$^{-1}$, which should be somewhere in the range of 40-100 M$^{-1}$ (Moore et al., *Proc. Natl. Acad. Sci. USA* 77:4509-13 (1980); Bruggemann et al., *Proc. Natl. Acad. Sci. USA* 83:4273-6 (1986)), with little or no deviation from linearity (Eftink et al., *Anal. Biochem.* 114:199-227 (1981)). In one experiment, K was determined as 60 M$^{-1}$ for ANTS/Tl$^+$ in a 150 mM TlNO$_3$/NaNO$_3$ ionic solution at pH 7.0. For the results from the above data set see FIG. 6.

Stock quencher solution was made of 150 mM TlNO$_3$ 10 mM HEPES at pH 7.0 in water. Stock buffer solution was made of 150 mM NaNO$_3$ 10 mM HEPES at pH 7.0 in water. HNO$_3$ or NaOH was used to adjust pH. The spectrophotometer was properly calibrated and normalized and, for at least one measurement, a full spectral sweep was done to verify that the ANTS excitation maximum is close to 370 nm.

EXAMPLE 7

Effects of the Bilayer Modifier Capsaicin

This Example describes experiments conducted to examine the effect of capsaicin on bilayer properties, as an example of a bilayer modifying amphiphile. Capsaicin, the active component in chili pepper, is a promiscuous ion channel modulator and alters lipid bilayer material properties, as demonstrated using single channel gA measurements (Lundbæk et al., *Mol. Pharmacol.* 68:680-9 (2005)).

Figure 7:
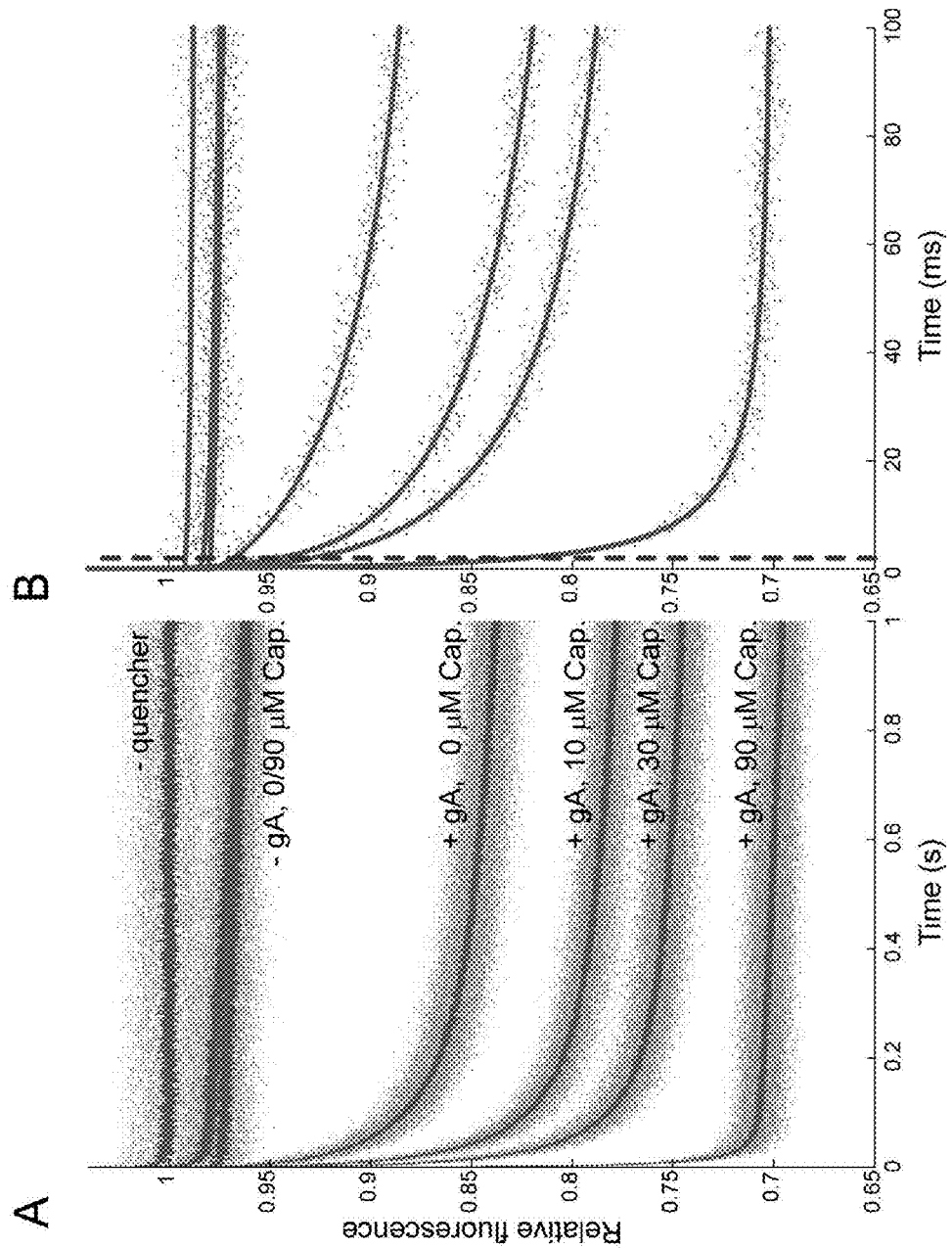
FIG. 7. The effect of capsaicin on $Tl^+$ influx rates—as deduced from quenching of the fluorescence signal recorded from ANTS-filled vesicles. The top three traces show results obtained in the absence of gA, with buffer only (no $Tl^+$) and with quencher in the presence and absence of 90 µM capsaicin. The four lower traces show results obtained in with 260 nM gA in the presence of quencher, from top to bottom; without and with 10, 30 and 90 µM capsaicin. A) 1 s traces; dots denote results from all individual repeats (n>5 per condition); solid lines within dots denote the average of all repeats. B) 100 ms traces; dots are from an individual repeat; solid lines within dots are stretched exponential fits (2-100 ms) to those repeats. The stippled vertical line denotes the 2 ms mark (the instrumental dead time).

FIG. 7 shows the effect of capsaicin using the gA based fluorescence assay. At μM concentrations capsaicin, by itself, did not increase Tl$^+$ permeability. FIG. 7, curves two and three from top, show that the time course of fluorescence quenching was comparable in the absence and presence of 90 μM capsaicin; capsaicin did not increase the amount of external ANTS (rupture vesicles) or promote Tr leak across vesicles membrane. In the presence of gramicidin capsaicin increased the rate of fluorescence quenching (Tl$^+$ influx) in a concentration dependent manner. FIG. 7, curves four to seven, show the rate of fluorescence in the presence of 0, 10, 30 and 90 μM capsaicin, respectively. The rates of quencher influx for 0, 10, 30 and 90 μM capsaicin with 260 nM gA, as determined by the rate of a stretched exponential (see Example 4), were 36±6, 69±6, 85±8 and 247±27 (mean±SD, n>10), respectively.

The results indicate that capsaicin partitions into the lipid bilayer and changes the bilayer material properties, lowering the energetic cost of the bilayer hydrophobic adaptation to the gA channel (see FIG. 1). The lowered energetic cost of bilayer deformation increases the gramicidin channel lifetime and appearance frequency (time-averaged surface density of conducting gA channels), leading to faster time course of fluorescence quenching.

EXAMPLE 8

Comparison to Single-Channel Method

To validate this approach, the following compounds were tested using the fluorescence-based gA method to compare with previous results from single-channel experiments of drugs and phytochemicals: genistein, genistin (Hwang et al., *Biochemistry* 42:13646-58 (2003)), (−)-epicatechin (EC), (−)-epigallocatechin gallate (EGCG) (Adachi et al., *Cancer Res.* 67:6493-501 (2007)), capsazepine, capsaicin (Lundbæk et al., *Mol. Pharmacol.* 68:680-9 (2005)), β-octyl-glucoside (β-OG) and Triton X100 (Lundbæk et al., *Biochemistry* 35:3825-30 (1996)) and (Lundbæk et al., *J. Gen. Physiol.* 123:599-621 (2004)); results for DMSO based on unpublished data from Shemille A. Collingwood, results for Gd$^{3+}$ based on data from Tashalee R. Brown; and results for Mefloquine from E. A. Hobart.

Figure 8:
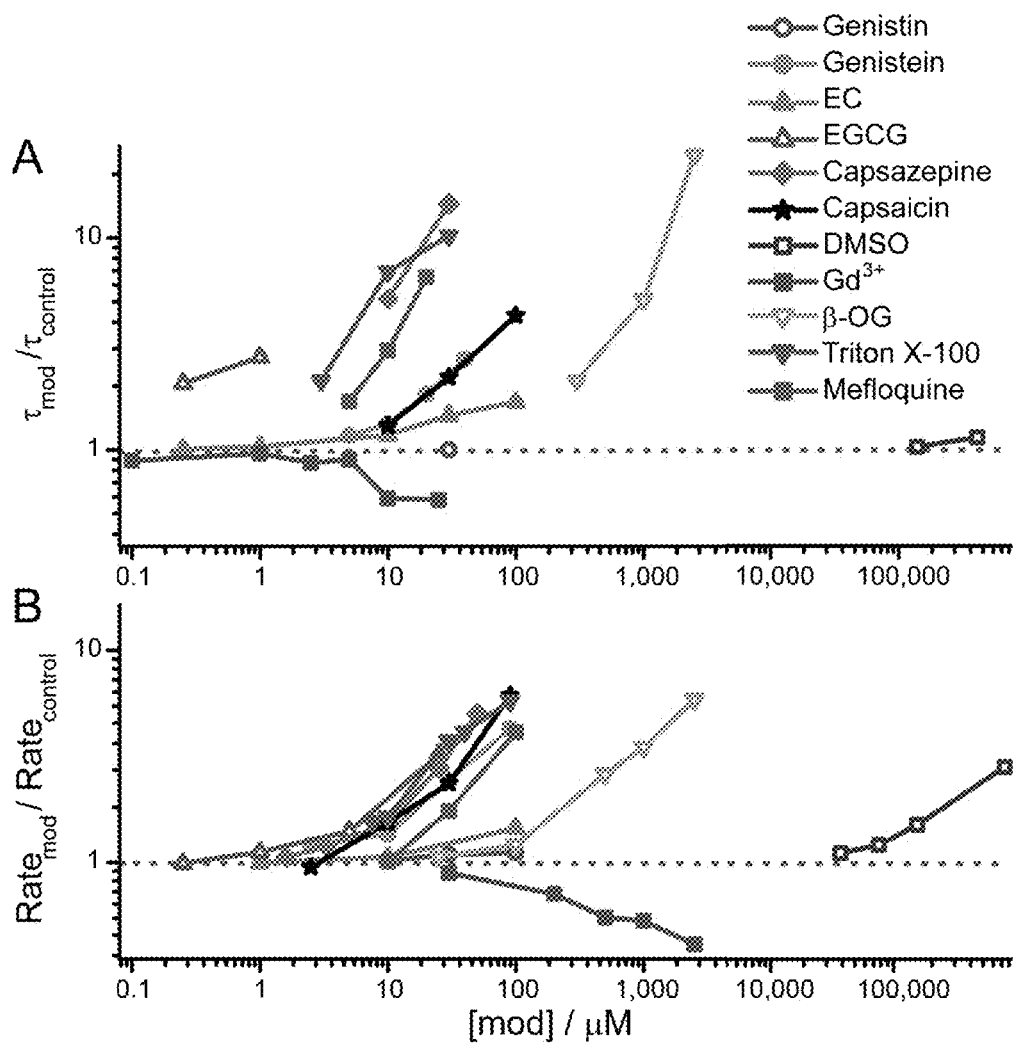
FIG. 8. Validating the stopped-flow fluorescence quench assay. A) The relative change in gA lifetime as a function of modifier concentration. Results from electrophysiological single channel recordings. Channel lifetimes are from (Lundbaek et al., *Biochemistry* 35:3825-30 (1996); Hwang et al., *Biochemistry* 42:13646-58 (2003); Lundbæk et al., *Mol. Pharmacol.* 68:680-9 (2005); Adachi et al., *Cancer Res.* 67:6493-501 (2007)); results for DMSO are based on unpublished data by Shemille A. Collingwood, Weill Cornell Medical College, results for $Gd^{3+}$ are based on unpublished data by Tashalee R. Brown and E. Ashley Hobart, Weill Cornell Medical College. B) The relative change in the Tr influx rate as a function of modifier concentration. The rate of $Tl^+$ influx is estimated as the rate of decay, evaluated at 2 ms, as determined from fitting a stretched exponential (Berberan-Santos et al., *Chem. Physics* 315:171-82 (2005)) to the time course of fluorescence quenching.

FIG. 8A shows the change in gA channel lifetimes (measured in single-channel experiments), FIG. 8B shows the change in gA activity as measured by relative change in the rate of fluorescence quenching. For all compounds, the highest concentration used was also tested in the absence of gA; none of the compounds induced significant change in the quencher membrane permeability or destabilized vesicles. For comparison of compounds properties and affinity to alter bilayer properties see Table 1.

When comparing the compounds' "active" concentrations—the concentration needed to half or double the rate of the fluorescence quenching or gA channel lifetime—it is worth noting that the biggest discrepancies arose with compounds that a priori would be expected to show differences between the two assays. The green tea phytochemical EGCG is a potent modifier of gA channel lifetime but it also causes conductance flickers or sub-conductance states. These flickers reduce ion flow through open gA channels and would therefore be expected to reduce rate of the fluorescence quenching, diminishing the effect of EGCG in the fluorescence assay. Mefloquine is measured as less "active" in the fluorescence assay than the changes in gA lifetime would indicate, but using single-channel electrophysiology it has also been shown that mefloquine decreases gA channel frequency. This results in a smaller increase in K$_D$ and therefore has less of an effect on the quencher influx rate. Gd$^{3+}$ is a negative curvature promoter and is expected to act differently depending on bilayer thickness/composition. In the single-channel assay the bilayers were made from DC$_{18:1}$PC/n-decane whereas the LUV in the fluorescence assay were made from DC$_{22:1}$PC lipids. In general, the "active" concentration tends to be slightly higher in the fluorescence assay.

TABLE 1

Modifiers tested and the concentrations at which they alter bilayer properties.

| Name | MW | cLogP | Single channel | Flourescence | Lipids/drug |
|---|---|---|---|---|---|
| β-octylglucoside | 292 | 0.1 | 270 | 325 | 2600 |
| Capsaicin | 305 | 3.5 | 25 | 21 | 25 |
| Capsazepine | 377 | 4.3 | 4 | 16 | 15 |
| Dimethyl sulfoxide | 78 | −1.4 | >410,000 | 340,000 | 90 |
| Epicatechin | 290 | 1.8 | 120 | 222 | 80 |
| Epigallocatechin gallate | 458 | 3.4 | 0.25 | 12 | 50 |
| Gd$^{3+}$ | 157 | | >30 | <1000 | |
| Genistein | 270 | 3.5 | 25 | 22 | 25 |
| Genistin | 432 | 0.8 | >>30 | 910 | 200 |

TABLE 1-continued

Modifiers tested and the concentrations at which they alter bilayer properties.

| Name | MW | cLogP | Single channel | Flourescence | Lipids/drug |
|------|-----|-------|----------------|--------------|-------------|
| Triton X-100 | ~640 | 2.8 | 9 | 13 | 170 |
| Mefloquine | 387 | 4 | 6 | 37 | 8 |

MW is the molecular weight.
cLogP, calculated octanol/water partitioning, values were obtained using the logP plug-in in MarvinSketch based on (Viswanadhan et al., *J Chem Inf Comput Sci.* 29: 163-72 (1989)).
Single channel is the concentration at which the molecule in question double/half gA channel lifetime as measured using standard bilayer-punch electrophysiological methods (Andersen et al., *Biophys. J.* 41: 119-33 (1983); Durkin et al., *J. Mol. Biol.* 211: 221-34 (1990)).
Fluorescence is the concentration at which the molecules double/half the rate of the fluorescence quenching as determined by a fitted stretched exponential.
Lipids/drug is the number of lipids per molecule at their active concentration or $\sim 1/m_{AM}$ (the estimated molecules/lipid molar ratio in the membrane phase) at the concentration where the molecules double, or half, the rate of the fluorescence quenching.

EXAMPLE 9

Vesicles Differing in Bilayer Thickness

LUVs made from $DC_{18:1}PC$, $DC_{20:1}PC$ or $DC_{22:1}PC$ lipids were investigated.

FIG. 9 shows the time course of ANTS fluorescence quenching with different amounts of gA, panels A, B and C showing results with LUV vesicle populations made from $DC_{18:1}PC$, $DC_{20:1}PC$ and $DC_{22:1}PC$, respectively. Note different amounts of gA were added for the different vesicle populations, the numbers represent the amount of gA added, as µL of a 50 ng per mL gA stock solution.

$Tl^+$ permeability through the vesicles made from long-chain phospholipids was slower than through the vesicles made from short-chain lipids, see FIGS. 9A, B and C no gA results for $DC_{18:1}PC$, $DC_{20:1}PC$ and $DC_{22:1}PC$ respectively. $Tl^+$ membrane permeability was slow enough at the relevant time scale (100 ms) that the total amplitude, even for the shortest lipids ($DC_{18:1}PC$), did not amount to a significant portion of the total signal. The reason for using the longer acyl chain lipids ($DC_{20:1}PC$ and $DC_{22:1}PC$) in the implementation of the assay in the above examples was so it was possible to use native gramicidin from *Bacillus brevis* which were easily accessible in large volumes (Sigma). The native gramicidin from *Bacillus brevis* is mostly composed of (~80%) [Val$^1$]gA which forms dimers readily in thin bilayers, so in order to shift the monomer⇌dimer equilibrium in favor of the non-conducting state, thicker bilayers were used.

EXAMPLE 10

Neurotoxins

The stopped-flow method was used to examine a library of neurotoxins based on the marine snail venom BrMT (Kelley et al., *J. Biol. Chem.* 278:34934-42 (2003); Sack et al., *J. Gen. Physiol.* 123:685-96 (2004)). BrMT slows Shaker potassium channel activation, but it was unclear whether it acts by binding to the channels or by altering lipid bilayer properties, as it is quite hydrophobic.

In collaboration with Dr. Jon Sack, it was found that BrMT and a number of synthetic BrMT analogues altered lipid bilayer properties, but that the changes in potassium channel function that were caused by BrMT and its analogues could not be predicted from the changes in gA channel activity, as deduced from the stopped-flow experiments. These results suggest that the BrMT family of neurotoxins is likely to alter potassium channel function by direct channel-toxin interactions.

EXAMPLE 11

Library of Candidate Compounds to treat TB

In collaboration with Dr. Carl F. Nathan and Crystal Darby (Department of Microbiology and Immunology, WCMC), a library of molecules that disrupt pH homeostasis in *M. tuberculosis* (Mtb) were examined. The goal of the initial screen that led to the library was to identify compounds that inhibit the Rv3671c protein in Mtb, as this protein is essential for Mtb's ability to survive the acid stress in the macrophage phagocytosome (Vandal et al., *Nature Med.* 14:849-54 (2008)). With Rv3671c being a putative membrane protein, the aim of the gA-based screen was to identify the ability of a compound to alter lipid bilayer properties—on the assumption that compounds that had minimal bilayer-perturbing effects were most likely to act through direct interactions with a target protein, a hypothesis that was attractive but unproven.

Based on the gA-based screen, and a parallel screen using a fluorescent pH indicator to probe whether the compounds might disrupt Mtb pH homeostasis by being protonophores, about two-thirds of the compounds turned out to be unsuitable as lead compounds for drug development—which does not necessarily preclude their use as cell biological tools, as long as "off-target" effects are recognized.

What is claimed is:

1. An assay for measuring the effect of a test substance on a lipid bilayer, comprising:

providing vesicles composed of a lipid bilayer, a pair of an indicator and a monovalent cation, and gramicidin, wherein the vesicles encompass one member of the pair of the indicator and the monovalent cation, and comprise gramicidin in the lipid bilayer; wherein the lipid bilayer is formed using phospholipids selected from the group consisting of di-$C_{22:1}$-, di-$C_{20:1}$-, di-$C_{18:1}$-, 1-$C_{16}$-2-$C_{18:1}$-acyl chains, and combinations thereof, in the absence or presence of cholesterol; and wherein molecules of gramicidin present in the lipid bilayer are in a monomer-dimer equilibrium in favor of monomer;

treating at least a portion of the vesicles with said test substance;

exposing the vesicles to a solution containing the other member of the pair of the indicator and the monovalent cation, wherein movement of said monovalent cation across the lipid bilayer through a conducting gramicidin channel causes the indicator to generate a detectable signal, wherein said detectable signal is indicative of the rate of monovalent cation movement across the lipid bilayer and is indicative of the density of conducting gramicidin channels in the lipid bilayer;

comparing the detectable signal generated from the vesicles treated with the test substance with the detectable signal generated from the vesicles not treated with the test substance, wherein a difference in the detectable signals correlates with the effect of said test substance on said lipid bilayer; and determining the effect of said test substance on said lipid bilayer based on the comparison.

2. The assay of claim 1, wherein the indicator is a fluorophore.

3. The assay of claim 1, wherein said monovalent cation has a radius less than 2 Å.

4. The assay of claim 3, wherein said monovalent cation is selected from the group consisting of $Tl^+$, $H^+$ and combinations thereof.

5. The assay of claim 1, wherein said pair of the indicator and the monovalent cation is selected from the group consisting of fluorescein-5-(and -6)-sulfonate and $H^+$, benzothiazole coumarin acetate and $Tl^+$; and 8-aminonaphthalene-1,3,6-trisulfonic acid disodium salt (ANTS) and $Tl^+$.

6. The assay of claim 1, wherein the vesicles encompass an indicator.

7. The assay of claim 6, wherein the indicator is a fluorophore that fluoresces in the absence of said monovalent cation, and said detectable signal is fluorescence quenching in the presence of said monovalent cation.

8. The assay of claim 7, wherein said indicator is ANTS, and said monovalent cation is $Tl^+$.

9. The assay of claim 8, wherein fluorescence quenching is measured over time.

10. The assay of claim 9, wherein the measurements at different time points are fitted to a stretched exponential equation.

11. The assay of claim 10, wherein the rate of fluorescence quenching at the time point of 2 milliseconds (ms) is determined and used as the basis of said comparison.

12. The assay of claim 1, wherein the vesicles initially encompass the indicator.

13. An assay for measuring the effect of a test substance on a lipid bilayer, comprising:
 providing vesicles composed of a lipid bilayer, a pair of an indicator and a monovalent cation, and gramicidin, wherein the vesicles encompass the indicator or the indicator-monovalent cation pair, and the vesicles comprise gramicidin in the lipid bilayer; wherein the lipid bilayer is formed using phospholipids selected from the group consisting of di-$C_{22:1}$-, di-$C_{20:1}$-, di-$C_{18:1}$-, 1-di-$C_{16}$-2-$C_{18:1}$-acyl chains, and combinations thereof, in the absence or presence of cholesterol; wherein molecules of gramicidin present in the lipid bilayer are in a monomer-dimer equilibrium in favor of monomer;
 treating at least a portion of the vesicles with said test substance;
 exposing the vesicles to a solution containing either the monovalent cation of the indicator-monovalent cation pair, wherein movement of said monovalent cation in the solution across the lipid bilayer through a conducting gramicidin channel into the vesicles causes the indicator to generate a detectable signal, or no monovalent cation in the solution, wherein movement of said monovalent cation in the vesicles across the lipid bilayer through a conducting gramicidin channel out of the vesicles causes the indicator to generate a detectable signal.

14. The assay of claim 1, wherein the lipid bilayer is formed using phospholipids selected from the group consisting of di-$C_{18:1}$PC, di-$C_{20:1}$PC, di-$C_{22:1}$PC, and combinations thereof.

15. The assay of claim 1, wherein the lipid bilayer is formed using lipids selected from the group consisting of di-$C_{20:1}$PC, di-$C_{22:1}$PC, and combinations thereof.

16. The assay of claim 1, wherein the thickness of the bilayer is about 1 nm thicker than the length of a conducting gA channel.

* * * * *